US011851686B2

(12) United States Patent
Clarke et al.

(10) Patent No.: US 11,851,686 B2
(45) Date of Patent: Dec. 26, 2023

(54) METHANE MONOOXYGENASE ENZYMES

(71) Applicant: Industrial Microbes, Inc., Alameda, CA (US)

(72) Inventors: Elizabeth Jane Clarke, San Francisco, CA (US); Derek Lorin Greenfield, Kensington, CA (US); Noah Charles Helman, El Cerrito, CA (US); Stephanie Rhianon Jones, Berkeley, CA (US); Baolong Zhu, Johnston, IA (US)

(73) Assignee: Industrial Microbes, Inc., Alameda, CA (US)

( * ) Notice: Subject to any disclaimer, the term of this patent is extended or adjusted under 35 U.S.C. 154(b) by 0 days.

(21) Appl. No.: 17/461,102

(22) Filed: Aug. 30, 2021

(65) Prior Publication Data

US 2021/0403883 A1 Dec. 30, 2021

Related U.S. Application Data

(63) Continuation of application No. 16/629,018, filed as application No. PCT/US2018/071149 on Jul. 6, 2018, now abandoned.

(60) Provisional application No. 62/566,733, filed on Oct. 2, 2017, provisional application No. 62/542,838, filed on Aug. 9, 2017, provisional application No. 62/529,648, filed on Jul. 7, 2017.

(51) Int. Cl.

| | |
|---|---|
| ***C12N 9/02*** | (2006.01) |
| ***C12N 15/70*** | (2006.01) |
| ***C12N 15/75*** | (2006.01) |
| ***C12N 15/77*** | (2006.01) |

(52) U.S. Cl.
CPC .......... *C12N 9/0073* (2013.01); *C12N 15/70* (2013.01); *C12N 15/75* (2013.01); *C12N 15/77* (2013.01); *C12Y 114/13025* (2013.01)

(58) Field of Classification Search
None
See application file for complete search history.

(56) References Cited

PUBLICATIONS

Leahy et al., Evolution of the soluble diiron monooxygenases, FEMS Microbiol. Rev. 27, 2003, 449-79. (Year: 2003).*
Halsey et al., Site-Directed Amino Acid Substitutions in the Hydroxylase Subunit of Butane Monooxygenase from Pseudomonas butanovora: ,J. Bacteriol. 188, 2006, 4962-69. (Year: 2006).*
Srinivasan, A guide to the Michaelis-Menten equation, FEBS J. 289, 2022, 6086-98. (Year: 2022).*
Smith et al., Mutagenesis of soluble methane monooxygenase, Methods Enz. 495, 2011, 135-47. (Year: 2011).*
Scanlan et al., Involvement of MmoR and MmoG in the transcriptional activation of Soluble methane monooxygenase genes in Methylosinus trichosporium OB3b, FEMS Microbiol. Lett 301, 2009, 181-187. (Year: 2009).*
Lock et al., Mutagenesis and expression of methane monooxygenase to alter regioselectivity with aromatic substrates, FEMS Microbiol. Lett. 364, Jun. 30, 2017, 1-6. (Year: 2017).*
Uniprot, Accession No. Q83WK3, 2017, www.uniprot.org. (Year: 2017).*

* cited by examiner

*Primary Examiner* — Robert B Mondesi
*Assistant Examiner* — Todd M Epstein
(74) *Attorney, Agent, or Firm* — K&L Gates LLP

(57) ABSTRACT

Improved soluble methane monooxygenases and soluble methane monooxygenase systems are provided.

7 Claims, 1 Drawing Sheet

Specification includes a Sequence Listing.

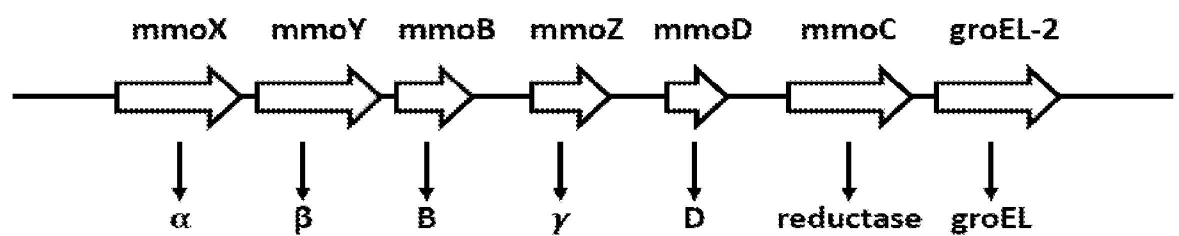
mmoX
mmoY
mmoB
mmoZ
mmoD
mmoC
groEL-2
α
β
B
γ
D
reductase
groEL

METHANE MONOOXYGENASE ENZYMES

PRIORITY CLAIM

This application claims priority to and the benefit as a continuation application of U.S. patent application Ser. No. 16/629,018 filed Jan. 6, 2020, which is the U.S. National Stage of International Application No. PCT/US20218/041149, filed Jul. 6, 2018; United States provision application 62/529,648, filed Jul. 7, 2017; U.S. provisional application 62/542,838 filed Aug. 9, 2017; and U.S. provisional application 62/566,733, filed Oct. 2, 2017, each of which is incorporated by reference herein in its entirety, including any drawings.

SEQUENCE LISTING SUBMISSION VIA EFS-WEB

A computer readable text file, entitled "Seq-list.txt", created on or about Jan. 6, 2020, with a file size of about 55,000 bytes contains the sequence listing for this application and is hereby incorporated by reference in its entirety.

Please insert the sequence listing into the specification.

This invention was made with government support under Department of Energy Agreement DE-AR0000432, awarded by the Advanced Research Projects Agency-Energy (ARPA-E). The government has certain rights in the invention.

FIELD

The technology provided herein relates to engineered enzymes applicable for industrial biotechnology. In particular, the technology relates to improved soluble methane monooxygenases and soluble methane monooxygenase systems.

BACKGROUND

Recent technological advances in synthetic biology have demonstrated the power and versatility of enzymatic pathways in living cells to convert organic molecules into industrial products. The petrochemical processes that currently manufacture these industrial products may be replaced by biotechnological processes that can often provide the same products at a lower cost and with a lower environmental impact. The discovery of new pathways and enzymes that can operate and be engineered in genetically tractable microorganisms will further advance synthetic biology.

Sugar, including simple sugars, starches, carbohydrates, and sugar alcohols, is often used as a raw material for biological fermentations. But, sugar is relatively expensive as a raw material, which severely limits the economic viability of any fermentation process that uses sugar as a raw material. When using biological fermentation to produce chemicals, companies often must limit themselves to the production of only select chemicals due to the high cost of sugar.

Other raw materials may be used to produce chemicals. Short alkanes, such as methane and ethane, are significantly less expensive as raw materials than sugar. Given the enormous supply of natural gas and the emergence of renewable methane-production technologies, short alkanes are expected to remain inexpensive for decades to come. Industrial products made by engineered microorganisms from short alkanes would be less expensive to manufacture than those made by sugar and should remain so for decades.

Any biological system capable of converting short alkanes into industrial products must include an enzyme that can activate the alkane. Naturally occurring bacteria that can activate methane use dioxygen to convert methane to methanol. An example of an enzyme capable of activating methane belongs to the class of enzymes known as soluble diiron monooxygenases.

There has been some difficulty expressing soluble diiron monooxygenases in industrially relevant hosts. There are many desirable factors involved in optimizing an enzyme for industrial use, such as high turnover rate, specificity for the desired substrate (and against any unintended substrates), solubility, high substrate binding affinity, reduced product inhibition, cofactor preference, and others. Successful functional expression of soluble diiron monooxygenases is critical for being able to use inexpensive raw materials in industrially relevant hosts.

What is needed is a soluble diiron monooxygenase with improved function that can be expressed in an industrially relevant host.

SUMMARY

The invention provided herein is drawn to improved soluble diiron monooxygenase mutants that can be functionally expressed in industrially relevant hosts.

Some embodiments provide at least one mutant soluble diiron monooxygenase system comprising at least one mutant subunit, wherein the at least one mutant subunit comprises one or more mutations, such that the activity of the mutant soluble diiron monooxygenase system is greater than the activity of a wild-type soluble diiron monooxygenase system.

In some embodiments, the at least one mutant soluble diiron monooxygenase system comprises a mutant hydroxylase alpha subunit, wherein the mutant hydroxylase alpha subunit comprises one or more mutations at one or more residue position(s): 3, 14, 25, 26, 32, 33, 35, 42, 44, 53, 54, 55, 56, 57, 61, 130, 135, 154, 162, 163, 168, 216, 251, 262, 263, 264, 277, 316, 322, 330, 347, 356, 374, 375, 381, 387, 393, 399, 405, 419, 420, 422, 431, 432, 433, 434, 434, 444, 453, 456, 459, 469, 470, 475, 480, 485, 493, 504, 505, 510, 513, 515, 525, and/or 526, wherein the residue position(s) are numbered with respect to SEQ ID NO: 3. In some embodiments, the one or more mutations comprises substitutions at one or more of residue position(s): L3P, L14P, A25S, Q26G, L32P, Q33K, Q33R, F35L, N42R, T44A, T44S, A53G, N54K, N54L, E55A, E55S, T56A, T56G, K57G, K57S, K57T, K61A, K61R, A130C, A130G, A130H, A130T, N135S, V154L, G162C, Q163F, H168G, L216M, Y251M, Y251W, A262E, S263Q, A264Q, T277G, I316S, G322N, R330T, Y347G, T356C, T356G, T356M, A374E, N375H, D381R, D381S, Y387I, Y387L, R393C, R399D, L405G, R419L, R419S, V420C, Q422E, K431E, G432A, A433G, A433Q, A433T, S434G, S434N, Q444E, G453V, M456V, A459E, I469V, F4701, G475*, E480G, L485E, K493E, K493V, D504E, K505E, D510E, K513R, K513T, L515G, A525Q, F526C, F526G, F526L, and/or F526S, wherein the residue position(s) are numbered with respect to SEQ ID NO: 3. In some embodiments, the one or more mutations consist of substitutions at residue position(s):

| | |
|---|---|
| a. | L3P; |
| b. | L3P, L14P; |
| c. | L3P, L14P, L32P, F35L, and R330T; |

-continued

| | |
|---|---|
| d. | L3P, L14P, and S434N; |
| e. | A25S; |
| f. | Q26G; |
| g. | L32P and A262E; |
| h. | Q33K; |
| i. | Q33R; |
| j. | N42R and T44A; |
| k. | T44S; |
| l. | A53G; |
| m. | N54K; |
| n. | N54L; |
| o. | E55A; |
| p. | E55S and N375H; |
| q. | T56A; |
| r. | T56G; |
| s. | K57G; |
| t. | K57S; |
| u. | K57T; |
| v. | K61A; |
| w. | K61R; |
| x. | A130C; |
| y. | A130C and R419L; |
| z. | A130H; |
| aa. | A130T; |
| ab. | N135S; |
| ac. | V154L; |
| ad. | V154L and S263Q; |
| ae. | G162C; |
| af. | Q163F; |
| ag. | H168G; |
| ah. | L216M; |
| ai. | Y251M; |
| aj. | Y251W; |
| ak. | A264Q; |
| al. | T277G; |
| am. | I316S; |
| an. | G322N; |
| ao. | Y347G; |
| ap. | T356C; |
| aq. | T356G; |
| ar. | T356M; |
| as. | A374E; |
| at. | D381R; |
| au. | D381S; |
| av. | Y387I; |
| aw. | Y387L; |
| ax. | R393C; |
| ay. | S399D; |
| az. | L405G; |
| ba. | R419S; |
| bb. | V420C; |
| bc. | Q422E, K431E, E480G, and D504E; |
| bd. | K431E; |
| be. | G432A; |
| bf. | A433G and A525Q; |
| bg. | A433Q; |
| bh. | A433T; |
| bi. | S434G and K505E; |
| bj. | S434N; |
| bk. | Q444E; |
| bl. | G453V; |
| bm. | M456V; |
| bn | A459E and K513T; |
| bo. | I469V; |
| bp. | F470I and G475*; |
| bq. | L485E; |
| br. | K493E; |
| bs. | K493V; |
| bt. | K505E; |
| bu. | D510E; |
| bv. | K513R; |
| bw. | K513T; |
| bx. | L515G; |
| by. | F526C; |
| bz. | F526G; |
| ca. | F526L; or |
| cb. | F526S, |

wherein the residue position(s) are numbered with respect to SEQ ID NO: 3.

In some embodiments, the at least one mutant soluble diiron monooxygenase system comprises a mutant accessory protein B, wherein the mutant accessory protein B comprises one or more mutations at one or more residue position(s): 3, 15, 16, 38, 58, 69, 81, 101, 102, 103, 106, 110, 112, 116, 118, 119, 120, 124, 126, 130, 131, 134, 136, 138, and/or 139, wherein the residue position(s) are numbered with respect to SEQ ID NO: 6. In some embodiments, the one or more mutations comprises substitutions at one or more residue position(s): V3G, L15M, K16G, V38G, T58E, N69K, A81G, N101G, V102A, V102L, Y103H, L106V, S110A, T112G, T112V, A116S, A116T, T118E, T118G, L119E, G120A, G120E, T124C, T124G, T126S, M130D, M130V, G131S, R134A, R134G, R134W, L136A, D138S, Y139G, Y139S, and/or Y139V, wherein the residue position(s) are numbered with respect to SEQ ID NO: 6. In some embodiments, the one or more mutations consists of a substitution at residue position(s):

| | |
|---|---|
| a. | V3G; |
| b. | L15M; |
| c. | K16G; |
| d. | V38G; |
| e. | T58E and T118E; |
| f. | N69K; |
| g. | A81G; |
| h. | N101G; |
| i. | V102A; |
| j. | V102L; |
| k. | Y103H; |
| l. | L106V; |
| m. | S110A; |
| n. | T112G; |
| o. | T112V; |
| p. | A116S; |
| q | A116T; |
| r. | T118G; |
| s. | L119E; |
| t. | G120A; |
| u. | G120E; |
| v. | T124C; |
| w. | T124G; |
| x. | T126S; |
| y. | M130D; |
| z. | M130V; |
| aa. | G131S; |
| ab. | R134A; |
| ac. | R134G; |
| ad. | R134W; |
| ae. | L136A; |
| af. | D138S; |
| ag. | Y139G; |
| ah. | Y139S; or |
| ai. | Y139V, |

wherein the residue position(s) are numbered with respect to SEQ ID NO: 6.

In some embodiments, the at least one mutant soluble diiron monooxygenase system comprises a mutant reductase subunit C, wherein the mutant reductase subunit C further comprises one or more mutations at one or more residue position(s): 17, 28, 38, 44, 45, 49, 58, 62, 64, 69, 74, 87, 90, 97, 98, 100, 110, 111, 116, 119, 125, 133, 135, 138, 143, 144, 152, 153, 155, 157, 174, 180, 184, 191, 196, 204, 208, 209, 211, 213, 216, 222, 235, 236, 238, 240, 242, 243, 244, 245, 246, 279, 281, 286, 288, 308, 324, 329, and/or 330, wherein the residue position(s) are numbered with respect to SEQ ID NO: 7. In some embodiments, the one or more mutations comprises substitutions at one or more residue position(s): L17R, L17Q, I28G, L38G, E44G, E44R, G45R, T49L, D58K, K62L, C64A, C64Q, L69A, E74R, K87L, L90Q, T97V, H98G, R100G, E110R, A111V, L116V, V119C, Q125L, D133V, C135T, R138Q, E143K, P144C, I152S, P153H, T155A, V157R, E174A, L180S, R184G, N191D, G196V, P204S, F208Q, G209W, K211V, R213G, A216V, A222G, R235G, Q236M, Q238G, W240E, A242V, P243G, N244G, E245D, E245M, T246M, C279S, W281R, D286T, E288V, N308V, C324G, S329G, and/or R330W, wherein the residue position(s) are numbered with respect to SEQ ID NO: 7. In some embodiments, the one or more mutations consist of a substitution at residue position(s):

| | |
|---|---|
| a. | L17R and W240E; |
| b. | L17Q; |
| c. | I28G; |
| d. | L38G; |
| e. | E44R; |
| f. | E44G; |
| h. | G45R and S329G; |
| i. | T49L; |
| j | D58K; |
| k. | K62L; |
| l. | C64Q; |
| m. | C64A and R330W; |
| n. | L69A; |
| o. | E74R; |
| p. | K87L and Q236M; |
| q. | L90Q and A216V; |
| r. | T97V; |
| s | H98G; |
| t. | R100G and E288V; |
| u. | E110R and N308V; |
| v. | A111V; |
| w. | L116V and K211V; |
| x. | V119C; |
| y. | Q125L; |
| z. | D133V and D286T; |
| aa. | C135T; |
| ab. | R138Q and F208Q; |
| ac. | E143K and P144C; |
| ad. | I152S; |
| ae. | P153H; |
| af. | T155A and C279S; |
| ag. | V157R; |
| ah. | L180S; |
| ai. | R184G; |
| aj. | N191D; |
| ak. | N196V; |
| al. | P204S; |
| am. | G209W; |
| an. | R213G and W281R; |
| ao. | A222G; |
| ap. | R235G; |
| aq. | Q238G; |
| ar. | A242V; |
| as. | P243G and E245D; |
| at. | N244G; |
| au. | E245M; |
| av. | T246M; or |
| aw. | C324G, |

wherein the residue position(s) are numbered with respect to SEQ ID NO: 7.

In some embodiments, the at least one mutant soluble diiron monooxygenase system comprises a mutant hydroxylase beta subunit, wherein the mutant hydroxylase beta subunit comprises one or more mutations at one or more residue position(s): 32, 36, 46, 47, 58, 64, 87, 93, 109, 133, 143, 146, 151, 155, 157, 160, 162, 202, 167, 182, 183, 184, 186, 201, 202, 203, 204, 206, 208, 209, 211, 212, 213, 214, 216, 217, 220, 222, 224, 225, 226, 230, 233, 236, 239, 242, 244, 250, 256, 260, 266, 269, 270, 272, 273, 276, 281, 291, 303, 304, 305, 306, 308, 310, 311, 314, 318, 322, 325, 328, 329, 330, 333, 335, 336, 356, 364, and/or 372, wherein the residue position(s) are numbered with respect to SEQ ID NO: 4. In some embodiments, the one or more mutations comprises substitutions at one or more residue position(s): N32V, G36L, L46V, T47H, T47V, P58N, A64G, T87V, V93G, Y109A, Y109E, Y109F, Y109V, I133S, E143T, N146R, A151G, N155G, Y157W, F160K, F160M, F160T, F160V, A162T, 202, A167Q, W182M, G183A, G183S, F184S, K186N, A201G, K202A, K202Q, K202R, K202S, I203V, V204S, G206E, D208A, E209R, T211I, A212G, V213G, V213W, P214V, A216G, E217L, N220V, E222R, Y224M, K225G, S226G, A230G, G233L, G233R, G233W, Q236G, Q236V, Q236W, F239L, N242G, N242P, N242V, S244G, A250C, F256W, V260C, Q266V, A269G, P270R, F272K, G273T, G273V, L276V, I281G, A291T, L303G, G304A, D305A, D305G, D305L, D305R, D305W, D306E, D306Q, D306R, E308G, S310R, S310W, D311A, D311G, R314G, R314H, R314Q, R318G, R318I, G322R, L325G, T328G, I329W, A330R, R333V, F335G, M336G, L356G, I364G, and/or D372W, wherein the residue position(s) are numbered with respect to SEQ ID NO: 4. In some embodiments, the one or more mutations consist of a substitution at residue position(s):

| | |
|---|---|
| a. | N32V; |
| b. | G36L; |
| c. | L46V; |
| d. | T47H and A151G; |
| e. | T47V; |
| f. | P58N; |
| g. | A64G; |
| h. | T87V; |
| i. | V93G; |
| j. | Y109A; |
| k. | Y109E; |
| l. | Y109F; |
| m. | Y109V; |
| n. | I133S; |
| o. | E143T; |
| p. | N146R; |
| q | N155G; |
| r. | Y157W; |
| s. | F160K; |
| t. | F160M; |
| u. | F160T; |
| v. | F160V; |
| w. | A162T and K202Q; |
| x. | A167Q; |
| y. | W182M; |
| z. | G183A; |
| aa. | G183S; |
| ab. | F184S; |
| ac. | K186N; |
| ad. | A201G and G233R; |
| ae. | K202A; |
| af. | K202R and A203G; |
| ag. | K202S; |
| ah. | I203V and G273T; |
| ai. | V204S; |
| aj. | G206E; |
| ak. | D208A and R318I; |
| al. | E209R; |
| am. | T211I; |
| an. | A212G and A330R; |
| ao. | A212G; |
| ap. | V213G; |
| aq. | V213W; |
| ar. | P214V; |
| as. | A216G and G273V; |
| at. | E217L; |
| au. | N220V; |
| av. | E222R and D305L; |
| aw. | Y224M; |
| ax. | K225G and R333V; |
| ay. | S226G; |
| az. | G233L; |
| ba. | G233W; |
| bb. | Q236G; |
| bc. | Q236V; |
| bd. | Q236W; |

-continued

| | |
|---|---|
| be. | F239L; |
| bf. | N242G; |
| bg. | N242P and A291T; |
| bh. | N242V; |
| bi. | S244G and I281G; |
| bj. | A250C and L325G; |
| bk. | F256W; |
| bl. | V260C; |
| bm. | Q266V; |
| bn. | A269G; |
| bo. | P270R and D306Q; |
| bp. | F272K; |
| bq | L276V; |
| bs. | L303G; |
| bt. | G304A; |
| bu. | D305A; |
| bv. | D305G; |
| bw. | D305R; |
| bx. | D305W; |
| by. | D306E; |
| bz. | D306R; |
| ca. | E308G and R314H; |
| cb. | S310R; |
| cc. | S310W; |
| cd. | D311A; |
| ce. | D311G; |
| cf. | R314G; |
| cg. | R314Q, |
| ch. | R318G; |
| ci. | G322R; |
| cj. | T328G; |
| ck. | I329W; |
| cl. | F335G; |
| cm. | M336G; |
| cn. | L356G; |
| co. | I364G; or |
| cp. | D372W, |

wherein the residue position(s) are numbered with respect to SEQ ID NO: 4.

In some embodiments, the at least one mutant soluble diiron monooxygenase system comprises a mutant hydroxylase gamma subunit, wherein the mutant hydroxylase gamma subunit comprises one or more mutations at one or more residue position(s): 10, 17, 18, 20, 21, 23, 24, 27, 29, 31, 33, 34, 41, 43, 45, 46, 47, 50, 51, 52, 53, 56, 63, 66, 67, 70, 79, 80, 103, 112, 116, 117, 127, 129, 136, 144, 147, 153, 154, 156, 165, and/or 166, wherein the residue position(s) are numbered with respect to SEQ ID NO: 5. In some embodiments, the one or more mutations comprises substitutions at one or more residue position(s): D10R, D10V, N17F, N17W, K18A, K18E, A20G, Q21H, N23A, N23D, N23E, N23G, N23L, N23V, T24E, T24V, K27G, K27Q, K27R, A29G, M31W, K33V, Q34A, Q34K, T41G, F43K, F43S, F43V, N45G, S46G, S46I, Y47S, Y47T, D50G, N51G, N51V, D52G, Y53C, I56L, K63G, K63T, V66D, L67E, R70E, R70G, R70V, H79E, K80M, D103G, I112V, Q116S, I117L, Y127F, L129G, G136Q, G136S, N144D, N144G, N144V, Y147D, E153G, E154G, R156A, H165G, L166E, and/or L166G, wherein the residue position(s) are numbered with respect to SEQ ID NO: 5. In some embodiments, the one or more mutations consist of a substitution at residue position(s):

| | |
|---|---|
| a. | D10R; |
| b. | D10V; |
| c. | N17F; |
| d. | N17W; |
| e. | K18A; |
| f. | K18E; |
| g. | A20G; |

-continued

| | |
|---|---|
| h. | Q21H and I112V; |
| i. | N23A; |
| j. | N23D; |
| k. | N23E; |
| l. | N23G; |
| m. | N23L; |
| n. | N23L and A117L; |
| o. | N23V; |
| p. | T24E; |
| q | T24V and F43: |
| r. | K27G; |
| s. | K27Q; |
| t. | K27R; |
| u. | A29G; |
| v. | A29G and E154G; |
| w. | M31W; |
| x. | K33V; |
| y. | Q34A; |
| z. | Q34K; |
| aa. | T41G; |
| ab. | F43S; |
| ac. | F43V; |
| ad. | N45G; |
| ae. | S46G; |
| af. | S46I; |
| ag. | Y47S; |
| ah. | Y47T; |
| ai. | D50G; |
| aj. | N51G; |
| ak. | N51V; |
| al. | D52G; |
| am. | Y53C; |
| an. | I56L; |
| ao. | K63G; |
| ap. | K63T; |
| aq. | V66D; |
| ar. | L67E; |
| as. | R70E; |
| at. | R70G; |
| au. | R70V; |
| av. | H79E; |
| aw. | K80M; |
| ax. | D103G and L166E; |
| ay. | Q116S; |
| az. | Y127F; |
| ba. | L129G; |
| bb. | G136Q; |
| bc. | G136S; |
| bd. | N144D; |
| be. | N144G; |
| bf. | N144V; |
| bg. | Y147D; |
| bh. | E153G; |
| bi. | E154G; |
| bj. | R156A; |
| bk | H165G; or |
| bl. | L166G, |

wherein the residue position(s) are numbered with respect to SEQ ID NO: 5.

In some embodiments, the at least one mutant soluble diiron monooxygenase system comprises a mutant subunit D (mmoD), wherein the mutant subunit D further comprises one or more mutations at one or more residue position(s): 4, 5, 7, 8, 9, 10, 13, 14, 17, 18, 20, 21, 22, 24, 27, 40, 60, 74, 79, 80, 89, 90, 92, 93, and/or 96, wherein the residue position(s) are numbered with respect to SEQ ID NO: 8. In some embodiments, the one or more mutations comprises substitutions at one or more residue position(s): S4R, A5S, Q7G, P8G, F9G, F9G, S10R, A13E, D14R, F17G, F17G, E18R, P20G, R21L, P22R, A24G, F27V, T40R, E60Q, S74A, T79G, T79S, H80G, E89D, Q90S, A92P, P93A, and/or D96R, wherein the residue position(s) are numbered with respect to SEQ ID NO: 8. In some embodiments, the one or more mutations consist of a substitution at residue position(s):

| | |
|---|---|
| a. | S4R; |
| b. | A5S; |
| c. | Q7G; |
| d. | P&G; |
| e. | F9G; |
| f. | S10R; |
| g. | A13E; |
| h. | D14R; |
| i. | F17G; |
| j. | E18R; |
| k. | P20G; |
| l. | R21L; |
| m. | P22R; |
| n. | A24G; |
| o. | F27V; |
| p. | T40R; |
| q | E60Q; |
| r. | S74A; |
| s. | T79G; |
| t. | T79S; |
| u. | H80G; |
| v. | E89D; |
| w. | Q90S; |
| x. | A92P; |
| y. | P93A; or |
| z. | D96R, |

wherein the residue position(s) are numbered with respect to SEQ ID NO: 8.

In some embodiments, the at least one mutant soluble diiron monooxygenase system comprises a mutant protein folding chaperone groEL-2, wherein the mutant protein folding chaperone groEL-2 further comprises one or more mutations at one or more residue position(s): 109, 160, 168, 169, 171, 182, 187, 396, 405, 409, 438, 444, 461, 466, 478, 484, 485, 495, 522, 524, and/or 529, wherein the residue position(s) are numbered with respect to SEQ ID NO: 9. In some embodiments, the one or more mutations comprises substitutions at one or more residue position(s): A109E, A109P, G160A, D168V, A169S, G171P, Q182W, L187V, T396L, V405G, V405D, N409G, A438K, D444S, P461V, G466L, A478L, A478R, A484E, A484G, N485T, G495H, V522L, G524T, and/or T529G, wherein the residue position(s) are numbered with respect to SEQ ID NO: 9. In some embodiments, the one or more mutations consists of substitutions at residue position(s):

| | |
|---|---|
| a. | A109E; |
| b. | A109P; |
| c. | G160A; |
| d. | D168V; |
| e. | A169S; |
| f. | G171P; |
| g. | Q182W; |
| h. | L187V; |
| i. | T396L; |
| j. | V405G; |
| k. | V405D; |
| l. | N409G; |
| m. | A438K; |
| n. | D444S; |
| o. | P461V; |
| p. | G466L; |
| q | A478L; |
| r. | A478R; |
| s. | A484E; |
| t. | A484G; |
| u. | N485T; |
| v. | G495H; |
| w. | V522L; |
| x. | G524T; or |
| y. | T529G, |

wherein the residue position(s) are numbered with respect to SEQ ID NO: 9.

In some embodiments, the at least one mutant soluble diiron monooxygenase system comprises or consists of one or more mutant subunits disclosed herein. In some embodiments, the at least one mutant soluble diiron monooxygenase system comprises or consists of one or more of a mutant hydroxylase alpha subunit, a mutant hydroxylase beta subunit, a mutant hydroxylase gamma subunit, a mutant accessory protein B, a mutant reductase subunit C, a mutant subunit D, and/or a mutant protein folding chaperone groEL-2 as disclosed herein.

A second aspect provides one or more isolated nucleic acids encoding one or more polypeptides or one or more subunits comprising or consisting of the mutant soluble diiron monooxygenase subunits or system disclosed herein. Some embodiments provide one or more vectors comprising or consisting of the one or more isolated nucleic acids. Some embodiments provide one or more host cells comprising or consisting of the one or more vectors. In some embodiments, the one or more host cells comprises a prokaryotic cell. In some embodiments, the prokaryotic cell comprises one or more of *Escherichia coli, Corynebacterium glutamicum*, and/or *Bacillus methanolicus*. In some embodiments, the one or more host cells comprises *Pichia pastoris* and/or *Saccharomyces cerevisiae.*

In some embodiments, at least one mutant soluble diiron monooxygenase system can be used to produce one or more chemicals. In some embodiments, the at least one mutant soluble diiron monooxygenase system comprises one or more mutant subunits as set forth herein, wherein the one or more mutant subunits is purified in vitro. In some embodiments, the at least one mutant soluble diiron monooxygenase system can be used in vitro to produce one or more chemicals.

BRIEF DESCRIPTION OF THE DRAWINGS

FIG. 1 sets forth a schematic overview of the soluble methane monooxygenase operon of *M. capsulatus* (Bath).

DESCRIPTION OF THE EXEMPLARY EMBODIMENTS

The present invention relates to at least one mutant soluble diiron monooxygenase system. The at least one mutant soluble diiron monooxygenase system may be composed of multiple subunits, each subunit comprising or consisting of one or more mutations. One or more mutations in any of the subunits improves activity.

I. Definitions

As used herein, "activity" or "enzyme activity" refers to moles of substrate converted per unit of time. Activity often depends upon conditions and the conditions are sometimes specified. For example, without limitation, activity can be measured using any of the assays set forth in the examples. In some embodiments, activity is measured as set forth in example 1. In some embodiments, activity is measured with respect to the amount of methanol a particular mutant soluble diiron monooxygenase produces as compared to a wild-type soluble diiron monooxygenase. In some embodiments, the at least one mutant soluble diiron monooxygenase system has an increased activity when compared to a wild-type soluble diiron monooxygenase system.

As used herein, the terms "protein folding chaperone," "folding chaperone," and "chaperone" refer to one or more proteins that improve the folding of polypeptide chains into 3-dimensional structures. Protein folding chaperones help their substrates, namely other proteins, become properly folded and often more highly soluble. Since most proteins must be folded in a particular shape to be functional, the expression of protein folding chaperones can assist in the proper assembly of certain enzymes in a cell and thereby can result in an increase in the enzymatic activity of the substrate proteins.

As used herein, "conservative amino acid substitution" refers to a substitution in which an amino acid residue is substituted by another amino acid residue having a side chain with similar chemical properties (e.g., charge or hydrophobicity.) In general, a conservative amino acid substitution should not substantially change the functional properties of a protein. The following six groups each contain amino acids that are often, depending upon context, considered conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

As used herein, "directed evolution" refers to a method used in protein engineering that mimics the process of natural selection to evolve proteins or nucleic acids toward a user-defined goal. Directed evolution comprises or consists of subjecting a gene to a method generating genetic diversity, assaying (screening or selecting) the diversity for a property of interest to identify beneficial, neutral, and/or deleterious mutations, and recombining of a subset of mutations which can then be screened for improved mutants.

As used herein, "enzyme" or "enzymatically" refers to biological catalysts. Enzymes accelerate, or catalyze, chemical reactions. Like all catalysts, enzymes increase the rate of reaction by lowering the activation energy.

As used herein, "eukaryotic" refers to organisms whose cells have a nucleus enclosed within membranes. Eukaryotes belong to the domain Eukaryota or Eukarya. Eukaryotic cells also contain other membrane-bound organelles such as mitochondria and the Golgi apparatus, and in addition, some cells of plants and algae contain chloroplasts.

As used herein, "homology" or "homologous" refers to the degree of biological shared ancestry in the evolutionary history of life. Homology or homologous may also refer to sequence homology, the biological homology between protein or polynucleotide sequences with respect to shared ancestry as determined by the closeness of nucleotide or protein sequences. Homology among proteins or polynucleotides is typically inferred from their sequence similarity. Alignments of multiple sequences are used to indicate which regions of each sequence are homologous. The term "percent homology" often refers to "sequence similarity." The percentage of identical residues (percent identity) or the percentage of residues conserved with similar physiochemical properties (percent similarity) e.g. leucine and isoleucine, is usually used to quantify homology. Partial homology can occur where a segment of the compared sequences has a shared origin.

Homology also refers to multi-gene homology. Thus, homology can also occur with respect to operons or gene clusters as basic units, instead of single genes. Homology can also occur with respect to a system of proteins instead of a single protein. One skilled in the art would know how to use programs such as MultiGeneBlast, a comprehensive BLAST implementation, to perform homology searches on multigene modules (See, Medema, H., Takano, E., and Breitling R., Detecting Sequence Homology at the Gene Cluster Level with MultiGeneBlast, Mol Biol Evol. (2013) May; 30(5): 1218-1223, which is incorporated by reference herein in its entirety, including any drawings). In a multigene homology, one skilled in the art can search for all genomic loci containing a combination of certain genes within the same gene cluster or for only certain genes or proteins of interest performing a specified part or combination of enzymatic steps. As it refers to a multi-subunit protein complex, "percent identity" is intended to mean the maximum value for the percent identity between any pairwise combination of amino acid sequences, calculated between all the subunits in one complex measured against all the subunits in the second complex. The percent identity between two subunits can be calculated using publicly available computational tools, such as BLASTp from NCBI.

As used herein, "isolated," "isolating," or "isolate" refers to a process of purification of a nucleic acid from a sample using a combination of physical and chemical methods.

As used herein, "nucleic acid," "polynucleotide," or "oligonucleotide" each refer to one or more polymers of nucleic acids and include, but are not limited to, coding regions, which are transcribed or translated into a polypeptide or chaperone, appropriate regulatory or control sequences, controlling sequences, e.g., translational start and stop codons, promoter sequences, ribosome binding sites, polyadenylation signals, transcription factor binding sites, termination sequences, regulatory domains, and enhancers, among others. A polynucleotide need not include all of its relevant or even complete coding regions on a single polymer and the invention provided herein contemplates having complete or partial coding regions on different polymers.

As used herein, "mutant," "mutant subunit," or "mutations" refers to an alteration of the nucleotide sequence of a genome of an organism, virus, or extrachromosomal nucleic acid or other genetic elements.

As used herein, "polypeptide" refers to a polymer consisting of a number of amino-acid residues bonded together in a chain, forming part of (or the whole of) a protein molecule.

As used herein, "prokaryotic" refers to a microscopic single-celled organism that has neither a distinct nucleus with a membrane nor other specialized organelles. Prokaryotes include bacteria and cyanobacteria.

As used herein, "soluble diiron monooxygenase" refers to a class of enzymes and enzyme complexes characterized by a catalytic core of two iron atoms and the ability to utilize molecular oxygen to catalyze hydroxylation or epoxidation of hydrocarbon bonds. The enzymes typically require NADH or NADPH as an electron donor. The soluble diiron monooxygenases are usually composed of one or more components and are present in the cytoplasm of the cell. Soluble diiron monooxygenases include soluble methane monooxygenases, phenol hydroxylases, toluene monooxygenases, and alkene monooxygenases (See, Leahy et al., *Evolution of the Soluble Diiron Monoxygenases*, FEMS Microbiology Reviews, Vol. 27., p.449-479, 2003, which is incorporated by reference herein in its entirety, including any drawings).

As used herein, "soluble diiron monooxygenase system" refers to a system of proteins that comprises or consists of one or more subunits of a soluble diiron monooxygenase. As used herein, soluble diiron monooxygenase may also refer to, but need not, all components that increase the activity of the one or more subunits of the soluble diiron monooxygenase such as, for example, without limitation, one or more chaperone proteins such as one or more groEL2 proteins.

As used herein, "subunit" refers to protein molecule that assembles or coassembles with other protein molecules to form a protein complex or enzyme. The disclosure is intended to include some or all of the subunits from any microorganism or combination of microorganisms, as determined by one skilled in the art.

As used herein, "vector" refers a nucleic acid molecule used as a vehicle to artificially carry foreign genetic material into another cell, such as a host cell, where the foreign genetic material can be replicated and/or expressed in the host cell.

As used herein, "wild-type" or "WT" refers to a strain, gene, or characteristic that prevails among individuals in natural conditions. A wild-type may be contrasted against strains, genes, or characteristics that do not prevail among organisms in natural conditions, such as those from a mutant.

II. Soluble Diiron Monooxygenase

Some embodiments provide at least one mutant soluble diiron monooxygenase system comprising at least one mutant subunit, wherein the at least one mutant subunit comprises one or more mutations such that the activity of the at least one mutant soluble diiron monooxygenase system is greater than the activity of the wild-type soluble diiron monooxygenase system.

Methanotrophs consume methane as their major carbon source and have an essential role in the global carbon cycle by limiting escape of the greenhouse gas methane to the atmosphere. To oxidize methane to methanol, bacteria use soluble methane monooxygenases and particulate methane monooxygenases.

Bacterial multicomponent monooxygenases are exceptional in their ability to hydroxylate a broad spectrum of hydrocarbon substrates. Soluble monooxygenases, alkene mono-oxygenases, phenol hydroxylases, and alkene/aromatic monooxygenases belong to the bacterial multicomponent monooxygenase superfamily. Soluble diiron monooxygenases may also accept substrates other than alkanes, and in some cases, the enzymes might hydroxylate a wide range of molecules. One such substrate is the simplest alkene, ethylene (also known as ethene, $C_2H_4$), which can be converted into ethylene oxide. Similarly, propylene is converted into propylene oxide by soluble diiron monooxygenases. Soluble monooxygenases contain three protein components, a hydroxylase (MMOH, which is composed of three subunits, the alpha, beta, and gamma, as provided herein), a reductase (MMOR), and a regulatory protein (MMOB). MMOD and groEL2 are also required for optimal catalytic function.

Any mutant subunits disclosed herein may be used and may be mixed and matched with one another provided only that the at least one mutant soluble diiron monooxygenase system is improved. In some embodiments, the at least one mutant soluble diiron monooxygenase system comprises or consists one or more of mutant subunits disclosed herein. In some embodiments, the at least one mutant soluble diiron monooxygenase system comprises or consists of any one or more of a mutant hydroxylase alpha subunit, a mutant hydroxylase beta subunit, a mutant hydroxylase gamma subunit, a mutant accessory protein B, a mutant reductase subunit C, a mutant subunit D, and/or a mutant protein folding chaperone groEL-2.

In some embodiments, the at least one mutant soluble diiron monooxygenase system comprises or consists of at least one mutant subunit from one or more organisms. In some embodiments, the at least one mutant soluble diiron monooxygenase system comprises or consists of more than one subunits coming from one or more than one organism. In other words, any combination of mutant subunits from any organism may be used and the one or more organisms may be mixed and matched with one another provided only that the at least one mutant soluble diiron monooxygenase system is improved.

In some embodiments, the one or more organisms comprises or consists of one or more of *Methylococcus capsulatus* (Bath), *Methylocystis* sp. strain M, *Methylosinus trichosporium* OB3b, *Rhodococcus rhodochrous* B-276, *Ralstonia pickettii* PKO1, *Pseudomonas mendocina* KR1, *Xanthobacter* sp. Py2, *Pseudomonas* sp. strain JS150, and/or *Pseudomonas* sp. strain CF600. In some embodiments, the one or more organisms comprises or consists of one or more organisms from Table O.

TABLE O

| Gene | Size (aa) | Enzyme | % Identity | % Dissimilarity | % Gaps | Organism | Accession no. |
|---|---|---|---|---|---|---|---|
| mmoX | 527 | sMMO | — | — | — | *Methylococcus capsulatus* (Bath) | M90050 |
| mmoX | 526 | sMMO | 82.4 | 17.5 | 0.2 | *Methylocystis* sp. strain M | U81594 |
| mmoX | 525 | sMMO | 81.2 | 18.6 | 0.2 | *Methylosinus trichosporium* OB3b | X55394 |
| amoC | 501 | AMO | 34.2 | 61.6 | 4.3 | *Rhodococcus rhodochrous* B-276 | D37875 |
| tbuAl | 501 | T3MO | 17.9 | 74.2 | 7.9 | *Ralstonia pickettii* PKO1 | U04052 |
| tmoA | 500 | T4MO | 17.9 | 74.0 | 8.0 | *Pseudomonas mendocina* KR1 | M65106 |
| aamA | 497 | AMO | 17.9 | 73.8 | 8.2 | *Xanthobacter* sp. Py2 | AJ006979 |
| tbmD | 513 | T2MO | 17.4 | 74.8 | 7.8 | *Pseudomonas* sp. strain JS150 | L40033 |
| dmpN | 517 | PH | 17.0 | 73.7 | 9.3 | *Pseudomonas* sp. strain CF600 | M60276 |
| mmoY | 389 | sMMO | — | — | — | *Methylococcus capsulatus* (Bath) | M90050 |
| mmoY | 395 | sMMO | 60.0 | 38.5 | 1.5 | *Methylocystis* sp. strain M | U81594 |
| mmoY | 395 | sMMO | 58.7 | 39.7 | 1.5 | *Methylosinus trichosporium* OB3b | X55394 |

TABLE O-continued

| Gene | Size (aa) | Enzyme | % Identity | % Dissimilarity | % Gaps | Organism | Accession no. |
|---|---|---|---|---|---|---|---|
| amoA | 343 | AMO | 25.1 | 66.4 | 8.5 | *Rhodococcus rhodochrous* B-276 | D37875 |
| tbuA2 | 329 | T3MO | 15.4 | 78.5 | 6.1 | *Ralstonia pickettii* PKO1 | U04052 |
| dmpL | 331 | PH | 13.3 | 79.0 | 7.7 | *Pseudomonas* sp. strain CF600 | M60276 |
| tbmB | 336 | T2MO | 12.9 | 81.7 | 5.4 | *Pseudomonas* sp. strain JS150 | L40033 |
| tmoE | 327 | T4MO | 12.0 | 81.6 | 6.4 | *Pseudomonas mendocina* KR1 | M65106 |
| mmoB | 141 | sMMO | — | — | — | *Methylococcus capsulatus* (Bath) | M90050 |
| mmoB | 138 | sMMO | 65.7 | 32.9 | 1.4 | *Methylocystis* sp. strain M | U81594 |
| mmoB | 138 | sMMO | 65.7 | 32.9 | 1.4 | *Methylosinus trichosporium* OB3b | X55394 |
| tbuV | 104 | T3MO | 22.0 | 73.4 | 4.6 | *Ralstonia pickettii* PKO1 | U04052 |
| dmpM | 90 | PH | 20.6 | 72.2 | 7.2 | *Pseudomonas* sp. strain CF600 | M60276 |
| amoB | 117 | AMO | 20.2 | 74.2 | 5.6 | *Rhodococcus rhodochrous* B-276 | D37875 |
| tmoD | 103 | T4MO | 19.3 | 75.2 | 5.5 | *Pseudomonas mendocina* KR1 | M65106 |
| tbmC | 89 | T2MO | 18.8 | 74.0 | 7.3 | *Pseudomonas* sp. strain JS150 | L40033 |
| mmoC | 348 | sMMO | — | — | — | *Methylococcus capsulatus* (Bath) | M90050 |
| mmoC | 343 | sMMO | 50.1 | 47.8 | 2.0 | *Methylocystis* sp. strain M | U81594 |
| mmoC | 340 | sMMO | 41.8 | 51.4 | 6.8 | *Methylosinus trichosporium* OB3b | S81887 |
| amoD | 342 | AMO | 28.5 | 63.7 | 7.9 | *Rhodococcus rhodochrous* B-276 | D37875 |
| dmpP | 353 | PH | 25.8 | 65.8 | 8.4 | *Pseudomonas* sp. strain CF600 | M60276 |
| tmoF | 326 | T4MO | 25.5 | 64.8 | 9.7 | *Pseudomonas mendocina* KR1 | M95045 |
| tbmF | 355 | T2MO | 23.2 | 69.5 | 7.3 | *Pseudomonas* sp. strain JS150 | L40033 |
| tbuC | 334 | T3MO | 22.7 | 69.0 | 8.2 | *Ralstonia pickettii* PKO1 | U04052 |

In some embodiments, the one or more organisms comprises or consists of *Methylococcus capsulatus* (Bath) (See, Coufal, D.; Blazyk, J; Whittington, D; Wu, W.; Rosensweig, A.; and Lippard, S., Sequencing and Analysis of the *Methylococcus capsulatus* (Bath) soluble methane monooxygenase genes (2000) *Eur. J. Biochem.* 267, 2174-2185, which is incorporated by reference in its entirety herein, including any drawings). One of the most well-studied methane monooxygenases is from *Methylococcus capsulatus* (Bath). (See, for example, *Petroleum Biotechnology* by Vazquez-Duhalt and Quintero-Romero in 2004, which is incorporated by reference herein in its entirety, including any drawings). FIG. 1 sets forth a schematic overview of the soluble methane monooxygenase operon of *M. capsulatus.*

III. Hydroxylase

MMOH from *M. capsulatus* is approximately 245 kD and is a non-heme, oxo-bridged diiron catalytic cluster which catalyzes dioxygen-dependent oxidation-hydroxylation reactions within diiron centers. MMOH is a multi-subunit dimeric ($\alpha_2\beta_2\gamma_2$ or $\alpha_2\beta_2$) protein, where each $\alpha$-subunit hosts the diiron center. The carboxylate-bridged diiron center is the locus for $O_2$ activation and subsequent substrate hydroxylation/epoxidation. The diiron center is similar to those in the R2 subunit of ribonucleotide reductase, ferritin, stearoyl acyl carrier protein, desaturase, and the aging-related protein Clk1.

In some embodiments, the at least one mutant soluble diiron monooxygenase system comprises a mutant hydroxylase alpha subunit. In some embodiments, the at least one mutant soluble diiron monooxygenase system comprises a mutant hydroxylase beta subunit. In some embodiments, the at least one mutant soluble diiron monooxygenase system comprises a mutant hydroxylase gamma subunit.

The hydroxylase alpha, hydroxylase beta, and hydroxylase gamma proteins are also referred to as MMOX, MMOY, MMOZ, respectively. The hydroxylase alpha protein from *M. capsulatus* is approximately 60.6 kD. The hydroxylase beta protein from *M. capsulatus* is approximately 45.1 kD. The hydroxylase gamma protein from *M. capsulatus* is approximately 19.8 kD. The proteins are respectively encoded by the mmoX, mmoY, and mmoZ genes.

IV. The Regulatory Protein (Accessory Protein B)

In some embodiments, the at least one mutant soluble diiron monooxygenase system comprises a mutant accessory protein B. Accessory protein B from *M. capsulatus* is a 15.8 kD protein that acts without co-factors. The MMOB/DmpM family comprises monooxygenase components such as the methane monooxygenase (EC:1.14.13.25) regulatory protein B. The family also includes DmpM or Phenol hydroxylase (EC:1.14.13.7) protein component P2, a protein that lacks redox co-factors and is required for optimal turnover of phenol hydroxylase. When the accessory protein B is present at a low concentration, it converts methane monooxygenase from an oxidase to a hydroxylase and stabilizes intermediates required for the activation of dioxygen.

Accessory protein B is required to couple electron consumption with substrate hydroxylation at the catalytic diiron center of the hydroxylase. When accessory protein B binds the hydroxylase, it triggers simultaneous conformational changes that modulate oxygen and methane access as well as proton delivery to the diiron center. Accessory protein B binds to the "canyon" of the hydroxylase (Asp 36-Leu 129) and competitively inhibits binding of reductase subunit C.

V. The Reductase

In some embodiments, the at least one mutant soluble diiron monooxygenase system comprises a mutant reductase subunit C.

Reductase subunit C from *M. capsulatus* is a 38.4 kD protein. Electron transfer to the diiron(III) centers in the hydroxylase involves NADH reductions of an oxidized FAD cofactor to a hydroquinone form, followed by the ferredoxin domain sequentially shuttling two electrons from the reduced FAD cofactor to the diiron center in the hydroxylase (See, Electron Transfer Control in Soluble Methane Monooxygenase; Weixue Wang, Roxana E. Iacob, Rebecca P Luob, John R. Engen, and Stephen J. Lippard; *J. Am. Chem. Soc.,* 2014, 136 (27), pp 9754-9762, which is incorporated in its entirety herein, including any drawings). The isolated domains have stable structures and retain biochemical properties of the two domains in full-length reductase subunit C.

VI. Subunit D, MMOD

In some embodiments, the at least one mutant soluble diiron monooxygenase system comprises a mutant MMOD or mutant subunit D. The cluster of genes that encode for the three characterized protein components of the hydroxylase, accessory protein subunit B, and the reductase subunit C also contains an additional open reading frame, orfY, which codes for a protein, MMOD, of unknown function. Despite the fact that there is no known function of MMOD, mutations in MMOD can improve the activity of a monooxygenase. MMOD is expressed in a native organism although at significantly lower levels that other monooxygenase proteins. Cofactorless MMOD is a potent inhibitor of soluble monooxygenase activity and binds to hydroxylase with a similar affinity to that of accessory protein subunit B and the reductase subunit C.

VII. groEL-2

In some embodiments, the at least mutant one soluble diiron monooxygenase system comprises a mutant protein folding chaperone groEL-2. GroEL-2 belongs to the chaperonin family of molecular chaperones and is found in a large number of bacteria. The groEL-2 gene is often located in close proximity to the monooxygenase operon and groEL-2 probably has a special relationship to the methane monooxygenase. GroEL-2 is thought to be required for the proper folding of many proteins and some bacteria, including *M. capsulatus*, have more than one gene homologous to groEL-2. Within the cell, the process of groEL-2-mediated protein folding involves multiple rounds of binding, encapsulation, and release of substrate protein.

VIII. Directed Evolution

In some embodiments, the activity of the at least one mutant soluble diiron monooxygenase system is improved through directed evolution. Any method of directed evolution well-known to one skilled in the art is within the scope of the invention.

Directed evolution consists of iterations of three steps: generating genetic diversity, assaying (screening or selecting) the diversity for a property of interest to identify beneficial, neutral, and/or deleterious mutations, and recombining a subset of mutations which can then be screened for improved mutants. Genetic variants may be used as templates either for additional rounds of recombination of the subset of mutations or for the discovery of additional genetic diversity of the at least one mutant soluble diiron monooxygenase system. The methods used to generate genetic diversity, to assay the at least one mutant soluble diiron monooxygenase system, and to recombine the mutations may vary.

Many methods are available for the generation of genetic diversity in a DNA sequence: chemical mutagenesis, ultraviolet-light-induced mutagenesis, error-prone PCR, directed saturation mutagenesis, and others. Any combination of these methods may also be used according to the invention. In some embodiments, each mutation is measured for its effects on the activity of at least one mutant soluble diiron monooxygenase system, which may be measured along one or more features or dimensions. For example, amino acid sequence variants of the protein(s) can be prepared by mutations in the DNA. Methods for mutagenesis and nucleotide sequence alterations include, for example, Kunkel, (1985) Proc Natl Acad Sci USA 82:488-92; Kunkel, et al., (1987) Meth Enzymol 154:367-82; U.S. Pat. No. 4,873,192; Walker and Gaastra, eds. (1983) Techniques in Molecular Biology (MacMillan Publishing Company, New York) and the references cited therein. Guidance regarding amino acid substitutions not likely to affect biological activity of the protein is found, for example, in the model of Dayhoff, et al., (1978) Atlas of Protein Sequence and Structure (Natl Biomed Res Found, Washington, D.C.). Each of the above-cited references is incorporated by reference in its entirety herein, including any drawings.

Furthermore, any of the one or more nucleic acids or one or more vectors (or any others mentioned herein or any of the regulatory elements that control or modulate expression thereof) disclosed herein may be optimized by genetic/protein engineering techniques, such as directed evolution or rational mutagenesis. Directed evolution allows one of ordinary skill in the art to optimize the enzymes for expression and activity in yeast, bacteria, or any other suitable cell or organism.

Directed evolution is exemplified herein to discover mutations for soluble methane monooxygenase from *Methylococcus capsulatus* (Bath) when functionally expressed inside *E. coli* cells. As set forth in the examples, a large mutant library was cloned and assayed using a non-fluorescent substrate that became fluorescent when hydroxylated by the activity of the enzyme. Any mutant that displayed improved activity was reassayed using the same and/or additional methods or conditions. Improved variants were then subjected to DNA sequencing to identify the mutations that caused increased activity.

Once a group of clones was identified as having improved activity, clones were sequenced to identify mutation(s) that were generated. DNA can be sequenced using any technique known to one skilled in the art, such as, for example, without limitation, Sanger sequencing. Higher-throughput techniques, such as those offered by Illumina or Pacific Biosciences, may also be utilized.

In some embodiments, combinations of mutations that display desirable activity are combined to form at least one mutant soluble diiron monooxygenase system that has particularly favorable activity. Once the recombined mutants have been constructed, one can assay these variants using the same techniques that were used previously to assay the original mutant libraries or using other assays that measure the at least one mutant soluble diiron monooxygenase system's properties. The combinations can be tested either by deliberately constructing specifically desired clones or by recombining mutations randomly in a one pot reaction. Methods of DNA construction for recombination libraries are well-known to those skilled in the art and include a variety of techniques, including SOE PCR, transfer PCR, and Quikchange mutagenesis (Agilent Technologies).

IX. Nucleic Acids and Vectors and Integration

Some aspects provide one or more isolated nucleic acids encoding any of the soluble diiron monooxygenase systems provided herein. In some embodiments, the one or more nucleic acids comprise one or more vectors. In some embodiments, the one or more nucleic acids are integrated into host cells.

The one or more nucleic acids can be introduced into the one or more host cells by any method known to one of skill in the art without limitation (See, for example, Hinnen et al. (1978) Proc. Natl. Acad. Sci. USA 75:1292-3; Cregg et al. (1985) Mol. Cell. Biol. 5:3376-3385; Goeddel et al. eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY, each of which is incorporated by reference in its entirety herein, including any drawings). Exemplary techniques include, but are not limited to, spheroplasting, electroporation, PEG 1000 mediated transformation, and lithium acetate or lithium chloride mediated transformation. In some embodiments, the one or more vectors comprises or consists of an extrachromosomal plasmid. In some embodiments, the one or more vectors comprises or consists of a chromosomal integration vector that can integrate the nucleotide sequence into the chromosome of the one or more host cells.

Expression of the one or more nucleic acids or one or more vectors may be modified. For example, the copy number of the one or more nucleic acids or one or more vectors may be altered by modifying transcription. This can be achieved, for example, by modifying the copy number of the nucleotide sequence of the one or more nucleic acids or one or more vectors (e.g., by using or generating a higher or lower copy number expression vector comprising the nucleotide sequence, by introducing additional copies of the nucleotide sequence into the genome of the one or more host cells cell, or by genetically modifying, deleting, or disrupting the nucleotide sequence in the genome of the one or more host cells) by changing the order of coding sequences on a polycistronic mRNA of an operon, or by breaking up an operon into individual genes, each with its own control elements. The strength of a promoter, enhancer, or operator to which a nucleotide sequence is operably linked may also be manipulated, increased, decreased, or different promoters, enhancers, or operators may be introduced.

Alternatively, or in addition, the copy number of the one or more nucleic acids or one or more vectors may be altered by modifying the level of translation of an mRNA. This can be achieved, for example, by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of an enzyme, altering expression of rare codon tRNAs used in the biosynthesis of the enzyme, and/or increasing the stability of an enzyme, as, for example, via mutation of its coding sequence.

Expression of the one or more nucleic acids or one or more vectors may be modified or regulated by targeting particular genes. For example, without limitation, in some embodiments of the methods described herein, the one or more host cells is contacted with one or more nucleases capable of cleaving, i.e., causing a break at a designated region within a selected site. In some embodiments, the break is a single-stranded break, that is, one but not both strands of the target site is cleaved. In some embodiments, the break is a double-stranded break. In some embodiments, a break inducing agent is any agent that recognizes and/or binds to a specific polynucleotide recognition sequence to produce a break at or near a recognition sequence. Examples of break inducing agents include, but are not limited to, endonucleases, site-specific recombinases, transposases, topoisomerases, and zinc finger nucleases, and include modified derivatives, variants, and fragments thereof.

In some embodiments, the recognition sequence within a selected target site can be endogenous or exogenous to a cell's genome. When the recognition site is an endogenous or exogenous sequence, it may be a recognition sequence recognized by a naturally occurring or native break inducing agent. Alternatively, an endogenous or exogenous recognition site could be recognized and/or bound by a modified or engineered break inducing agent designed or selected to specifically recognize the endogenous or exogenous recognition sequence to produce a break. In some embodiments, the modified break inducing agent is derived from a native, naturally occurring break inducing agent. In other embodiments, the modified break inducing agent is artificially created or synthesized. Methods for selecting such modified or engineered break inducing agents are known in the art.

In some embodiments, the one or more nucleases is a CRISPR/Cas-derived RNA-guided endonuclease. CRISPR may be used to recognize, genetically modify, and/or silence genetic elements at the RNA or DNA level or to express heterologous or homologous genes. CRISPR may also be used to regulate endogenous or exogenous nucleic acids. Any CRISPR/Cas system known in the art finds use as a nuclease in the methods and compositions provided herein. CRISPR systems that find use in the methods and compositions provided herein also include those described in International Publication Numbers WO 2013/142578 A1, WO 2013/098244 A1 and Nucleic Acids Res (2017) 45 (1): 496-508, the contents of which are hereby incorporated in their entireties).

In some embodiments, the one or more nucleases is a TAL-effector DNA binding domain-nuclease fusion protein (TALEN). TAL effectors of plant pathogenic bacteria in the genus Xanthomonas play important roles in disease, or trigger defence, by binding host DNA and activating effector-specific host genes. (See, e.g., Gu et al. (2005) Nature 435:1122-5; Yang et al., (2006) Proc. Natl. Acad. Sci. USA 103:10503-8; Kay et al., (2007) Science 318:648-51; Sugio et al., (2007) Proc. Natl. Acad. Sci. USA 104:10720-5; Romer et al., (2007) Science 318:645-8; Boch et al., (2009)

Science 326(5959):1509-12; and Moscou and Bogdanove, (2009) 326(5959):1501, each of which is incorporated by reference in their entirety). A TAL effector comprises a DNA binding domain that interacts with DNA in a sequence-specific manner through one or more tandem repeat domains. The repeated sequence typically comprises 34 amino acids, and the repeats are typically 91-100% homologous with each other. Polymorphism of the repeats is usually located at positions 12 and 13, and there appears to be a one-to-one correspondence between the identity of repeat variable-diresidues at positions 12 and 13 with the identity of the contiguous nucleotides in the TAL-effector's target sequence.

The TAL-effector DNA binding domain may be engineered to bind to a desired sequence and fused to a nuclease domain, e.g., from a type II restriction endonuclease, typically a nonspecific cleavage domain from a type II restriction endonuclease such as FokI (See, e.g., Kim et al. (1996) Proc. Natl. Acad. Sci. USA 93:1156-1160, which is incorporated by reference in its entirety herein, including any drawings). Other useful endonucleases may include, for example, HhaI, HindIII, Nod, BbvCI, EcoRI, BglI, and AlwI. Thus, in preferred embodiments, the TALEN comprises a TAL effector domain comprising a plurality of TAL effector repeat sequences that, in combination, bind to a specific nucleotide sequence in a target DNA sequence, such that the TALEN cleaves the target DNA within or adjacent to the specific nucleotide sequence. TALENS useful for the methods provided herein include those described in WO10/079430 and U.S. Patent Application Publication No. 2011/0145940, which is incorporated by reference herein, including any drawings.

In some embodiments, the one or more of the nucleases is a zinc-finger nuclease (ZFN). ZFNs are engineered break inducing agents comprised of a zinc finger DNA binding domain and a break inducing agent domain. Engineered ZFNs consist of two zinc finger arrays each of which is fused to a single subunit of a non-specific endonuclease, such as the nuclease domain from the FokI enzyme, which becomes active upon dimerization.

Useful zinc-finger nucleases include those that are known and those that are engineered to have specificity for one or more sites. Zinc finger domains are amenable for designing polypeptides that specifically bind a selected polynucleotide recognition sequence. Thus, they are amenable to modifying or regulating expression by targeting particular genes.

The one or more nucleic acids or one or more vectors can be modified in a number of other ways, including, but not limited to, gene silencing or any other form of genetic modification, expressing a modified form of the one or more nucleic acids or one or more vectors that exhibits increased or decreased solubility in the one or more host cells, expressing an altered form of the expressed one or more nucleic acids or one or more vectors that lacks a domain through which the activity of the enzyme is inhibited, expressing a modified form of the expressed one or more nucleic acids or one or more vectors that has a higher or lower Kcat or a lower or higher Km for a substrate, or expressing one or more polypeptides from the one or more nucleic acids or one or more vectors that is more or less affected by feed-back or feed-forward regulation by another molecule in the pathway.

In some embodiments, the at least one mutant soluble diiron monooxygenase system is modified. It will be recognized by one skilled in the art that absolute identity to the at least one mutant soluble diiron monooxygenase system is not strictly necessary. For example, changes in a particular gene or polynucleotide comprising a sequence encoding a polypeptide or an enzyme can be performed and screened for activity. Such modified or mutated polynucleotides and polypeptides can be screened for expression or function using methods known in the art.

Those of skill in the art will recognize that, due to the degenerate nature of the genetic code, a variety of polynucleotides differing in their nucleotide sequences can be used for the at least one mutant soluble diiron monooxygenase system of the disclosure. Due to the inherent degeneracy of the genetic code, other polynucleotides that encode substantially the same or functionally equivalent polypeptides or subunits can also be used. The disclosure includes polynucleotides of any sequence that encode the amino acid sequences of the polypeptides and proteins of the enzymes utilized in the methods of the disclosure.

In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have an activity that is identical or similar to the referenced polypeptide. Accordingly, the at least one mutant soluble diiron monooxygenase system encoded by the one or more nucleic acids or one or more vectors shown herein merely illustrate embodiments of the disclosure.

The disclosure also includes at least one mutant soluble diiron monooxygenase system with different amino acid sequences than the specific monooxygenase systems described herein if the modified or variant polypeptides have an activity that is desirable yet different from referenced polypeptide. In some embodiments, the at least one mutant soluble diiron monooxygenase system may be altered by modifying the gene that encodes the at least one mutant soluble diiron monooxygenase system so that the expressed systems proteins are more or less active than the wild-type version.

As will be understood by those of skill in the art, it can be advantageous to modify a coding sequence to enhance expression in a particular host or one or more host cells. The genetic code is redundant with 64 possible codons, but most organisms typically use a subset of these codons. Codons can be substituted to reflect the preferred codon usage of the host, in a process sometimes called "codon optimization" or "controlling for species codon bias."

Optimized coding sequences containing codons preferred by a particular prokaryotic or eukaryotic hosts (See, for example, Murray et al., 1989, Nucl Acids Res. 17: 477-508, which is incorporated by reference in its entirety herein, including any drawings) can be prepared, for example, to increase the rate of translation or to produce recombinant RNA transcripts having desirable properties, such as a longer half-life, as compared with transcripts produced from a non-optimized sequence. Translation stop codons can also be modified to reflect preference in the one or more host cells. For example, typical stop codons for *S. cerevisiae* and mammals are UAA and UGA, respectively.

In addition, homologs of the at least one mutant soluble diiron monooxygenase system are encompassed by the disclosure. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences.

It is recognized that residue positions that are not identical often differ by conservative amino acid substitutions. In cases where two or more amino acid sequences differ from each other by conservative substitutions, the percent sequence identity or degree of homology may practically be adjusted upwards to correct for the conservative nature of the substitution. Means for making this adjustment are well known to those of skill in the art (See, e.g., Pearson W. R., 1994, Methods in Mol Biol 25: 365-89, which is incorporated by reference in its entirety herein, including any drawings).

Sequence homology and sequence identity for polypeptides is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

In addition, genes encoding enzymes homologous to the polypeptides encoded by the one or more nucleic acids or one or more vectors can be identified from other fungal and bacterial species or other species if they are orthologous or if there is homology between the two chosen species. Sources of prokaryotic enzymes that are useful include, but are not limited to, *Methylococcus capsulatus* (Bath), *Methylocystis* sp. strain M, *Methylosinus trichosporium* OB3b, *Rhodococcus rhodochrous* B-276, *Ralstonia pickettii* PKO1, *Pseudomonas mendocina* KR1, *Xanthobacter* sp. Py2, *Pseudomonas* sp. strain JS150, and/or *Pseudomonas* sp. strain CF600 or any of the one or more organisms from Table O.

Techniques known to those skilled in the art may be suitable to identify additional homologous genes and homologous enzymes. Generally, analogous genes and/or analogous enzymes can be identified by functional analysis and will have functional similarities. As an example, to identify homologous or analogous biosynthetic pathway genes, proteins, or enzymes, techniques may include, but are not limited to, cloning a gene by PCR using primers based on a published sequence of a gene/enzyme of interest or by degenerate PCR using degenerate primers designed to amplify a conserved region among a gene of interest.

Further, one skilled in the art can use other techniques to identify homologous or analogous genes, proteins, or enzymes with functional homology or similarity to any of mutant soluble diiron monooxygenase systems disclosed herein. Techniques include examining a cell or cell culture for catalytic activity (e.g. as described herein or in Kiritani, K., Branched-Chain Amino Acids Methods Enzymology, 1970, which is incorporated by reference in its entirety herein, including any drawings), then isolating the enzyme with the activity through purification, determining the protein sequence of the enzyme through techniques such as Edman degradation, design of PCR primers to the likely nucleic acid sequence, amplification of the DNA sequence through PCR, and cloning of the nucleic acid sequence. To identify homologous or similar genes and/or homologous or similar proteins, analogous genes and/or analogous proteins, techniques also include comparison of data concerning a candidate gene or enzyme with databases such as BRENDA, KEGG, or MetaCYC.

In some embodiments, the at least one mutant soluble diiron monooxygenase system comprises or consists of a mutant subunit having homology to any of the subunits disclosed herein. In some embodiments, the at least one mutant soluble diiron monooxygenase system comprises or consists of a mutant subunit having homology of at least about 80%, at least about 85%, at least about 90%, at least about 91%, at least about 92%, at least about 93%, at least about 94%, at least about 95%, at least about 96%, at least about 97%, at least about 98%, or at least about 99% homology to any of the mutant subunits disclosed herein. In some embodiments, the at least one mutant soluble diiron monooxygenase system comprises or consists of a system having homology of at least about 80%, at least about 85%, at least about 90%, at least about 91%, at least about 92%, at least about 93%, at least about 94%, at least about 95%, at least about 96%, at least about 97%, at least about 98%, or at least about 99% homology to any one or more of the subunits or groups of proteins disclosed herein.

The invention is not just limited to subunits and systems of *M. capsulatus* and subunits and systems other than those from *M. capsulatus* are intended to be within the scope of the invention. In some embodiments, the at least one mutant soluble diiron monooxygenase system comprises or consists of a mutant subunit from a species other than *M. capsulatus* having homology to any of the subunits disclosed herein. In some embodiments, the at least one mutant soluble diiron monooxygenase system comprises or consists of a mutant subunit from a species other than *M. capsulatus* having homology of at least about 80%, at least about 85%, at least about 90%, at least about 91%, at least about 92%, at least about 93%, at least about 94%, at least about 95%, at least about 96%, at least about 97%, at least about 98%, or at least about 99% homology to any of the mutant subunits disclosed herein. In some embodiments, the at least one mutant soluble diiron monooxygenase system comprises or consists of a system from a species other than *M. capsulatus* having homology of at least about 80%, at least about 85%, at least about 90%, at least about 91%, at least about 92%, at least about 93%, at least about 94%, at least about 95%, at least about 96%, at least about 97%, at least about 98%, or at least about 99% homology to any one or more of the subunits or groups of proteins disclosed herein.

X. Cells or Host Cells

Cells that can be used may be any cells deemed useful by those of skill in the art. Cells useful in the compositions and methods provided herein include archaeal, prokaryotic, or eukaryotic cells. The term cell and/or host cells may be interchangeable as used throughout this specification. Either a cell or host cell may be modified or unmodified and may comprise a host that is unmodified and has a native pathway.

In some embodiments, the one or more host cells comprises or consists of one or more prokaryotic cells. In some embodiments, the one or more host cells comprises or consists of any one of gram-positive, gram-negative, and/or gram-variable bacteria. Examples include, but are not limited to, cells belonging to the genera: *Actinobacillus, Agrobacterium, Alicyclobacillus, Anabaena, Anacystis, Anaerobiospirillum, Arthrobacter, Azobacter, Bacillus, Brevibacterium, Chromatium, Clostridium, Corynebacte-* rium, Enterobacter, Envinia, Escherichia, Gluconobacter, Klebsiella, Lactobacillus, Lactococcus, Mannheimia, Mesorhizobium, Methylobacterium, Microbacterium, Phormidium, Pseudomonas, Rhizobium, Rhodobacter, Rhodopseudomonas, Rhodospirillum, Rhodococcus, Salmonella, Scenedesmun, Serratia, Shigella, Staphlococcus, Streptomyces, Synnecoccus*, and *Zymomonas*. Examples of strains include, but are not limited to: *Actinobacillus succinogenes, Anaerobiospirillum succiniciproducens, Bacillus subtilis, Bacillus amyloliquefacines, Brevibacterium ammoniagenes, Brevibacterium immariophilum, Clostridium acetobutylicum, Clostridium beigerinckii, Enterobacter sakazakii, Escherichia coli, Gluconobacter oxydans, Klebsiella oxytoca, Lactobacillus plantarum, Lactococcus lactis, Mannheimia succiniciproducens, Mesorhizobium loti, Pseudomonas aeruginosa, Pseudomonas mevalonii, Pseudomonas fluorescens, Pseudomonas pudica, Rhizobium etli, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus, Streptomyces coelicolor*, and *Zymomonas mobilis.*

In some embodiments, the one or more host cells comprises or consists of archaeal cells. In some embodiments, archaeal cells include, but are not limited to: *Aeropyrum, Archaeglobus, Halobacterium, Methanococcus, Methanobacterium, Pyrococcus, Sulfolobus*, and *Thermoplasma*. Examples of archaea strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

In some embodiments, the one or more host cells comprises or consists of eukaryotic cells. In some embodiments, the eukaryotic cells include, but are not limited to, fungal cells, algal cells, insect cells, and plant cells. In some embodiments, yeasts useful in the present methods including yeasts that belong to the genera *Aciculoconidium, Ambrosiozyma, Arthroascus, Arxiozyma, Ashbya, Aspergillus, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the one or more host cells comprises or consist of at least one of *Escherichia coli, Bacillus subtilis, Bacillus methanolicus, Pseudomonas putida, Saccharomyces cerevisiae, Pichia pastoris, Pichia methanolica, Salmonella enterica, Corynebacterium glutamicum, Klebsiella oxytoca, Anaerobiospirillum succiniciproducens, Actinobacillus succinogenes, Mannheimia succiniciproducens, Rhizobium etli, Gluconobacter oxydans, Zymomonas mobilis, Lactococcus lactis, Lactobacillus plantarum, Streptomyces coelicolor, Clostridium acetobutylicum, Pseudomonas fluorescens, Schizosaccharomyces pombe, Kluyveromyces lactis, Kluyveromyces marxianus, Aspergillus terreus, Aspergillus niger*, and *Candida utilis*. In some embodiments, the one or more host cells comprises or consist of *Escherichia coli*. In some embodiments, the one or more host cells comprises or consists of *Pichia pastoris*. In some embodiments, the one or more host cells comprises or consists of *Saccharomyces cerevisiae*. In some embodiments, the one or more host cells comprises or consist of *Corynebacterium glutamicum*. In some embodiments, the one or more host cells comprises or consist of *Bacillus methanolicus.*

XI. Chemicals

In some embodiments, the at least one mutant soluble diiron monooxygenase system is expressed in a host cell for production or one or more chemicals. In some embodiments, the one or more chemicals comprises or consists of one or more of dicarboxylic acid, malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, isoprene, farnesene, farnesane, squalene, squalane, carotenoids, any or all of the amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, epoxides such as ethylene oxide and propylene oxide, ethanol, propanol, 1-butanol, 2-butanol, isobutanol (2-methylpropan-1-ol), alcohols, alkanes, alkenes, olefins, animal feed additives, mixtures of amino acids, and proteins. Other examples of chemicals include, but are not limited to, ethanol, propanol, isopropanol, butanol, fatty alcohols, fatty acid esters, ethyl esters, wax esters; hydrocarbons and alkanes such as propane, octane, diesel, Jet Propellant 8 (JP8); terephthalate, 1,3-propanediol, 1,4-butanediol, acrylate, adipic acid, c-caprolactone, isoprene, caprolactam, and polymers of these, plus other polymers, such as polyols, polyhydroxyalkanoates (PHA), poly-beta-hydroxybutyrate (PHB), rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid, chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest.

In some embodiments, the one or more chemicals comprises or consists of biofuels, industrial and specialty chemicals, intermediates used to make additional products, nutritional supplements, nutraceuticals, polymers, paraffin replacements, personal care products, and pharmaceuticals. In some embodiments, the one or more chemicals comprises or consists of natural and non-natural compounds such as, for example, amino acids, nucleic acids, nucleotides, polynucleotides and all related biological molecules, amino acids and nucleotides that are modified in a way differently than they are normally modified in biological systems (such as, for example, without limitation, non-natural amino acids).

In some embodiments, the one or more chemicals comprises or consists of methanol, ethanol, propanol, butanol, or naphthol. In some embodiments, the one or more chemicals comprises or consists of succinate, malate, fatty acids, lysine, and/or glutamate. In an embodiment, the one or more chemicals comprises or consist of 3-hydroxypropionate or a polymer of 3-hydroxypropionate. In some embodiments, the one or more chemicals consists of methanol.

In some embodiments, the at least one mutant soluble diiron monooxygenase system comprises one or more mutant subunits as set forth herein, wherein the one or more mutant subunits is purified in vitro. In some embodiments, the at least one mutant soluble diiron monooxygenase system can be used in vitro to produce one or more chemicals.

EXAMPLES

Example 1

Mutagenesis of the Hydroxylase Alpha Subunit

A saturation library of mutations in the mmoXgene in pBZ34 (SEQ ID NO: 1) was constructed using degenerate primers. The library was transformed into a strain of *E. coli* named NH283 (derived from the commercially available strain NEB Express via a deletion of the araBAD operon using a chloramphenicol resistance gene and the method of Datsenko and Wanner (2000)). The library was recovered in SOC for 1 hour at 37° C., 280 rpm, and then spread on LB agar plates supplemented with 100 μg/mL spectinomycin.

Colonies were picked into 96-well deep-well plates (Costar), containing 400 μL LB supplemented with 100 μg/mL spectinomycin. The plates were sealed with an air-permeable sealing tape and incubated shaking at 37° C., 270 rpm for about 16 hours. Each plate contained several wells with the strain BZ85 (NH283/pBZ34) as an on-plate control, against which all mutant colonies could be compared. After the 16-hour incubation, each well was subcultured into a fresh 96-well deep-well plate, using 25 μL inoculum into 250 μL of LB supplemented with 100 μg/mL spectinomycin, 1 mM L-arabinose, 50 μM ferric citrate, and 200 μM L-cysteine. These plates were sealed and incubated at 37° C., 270 rpm.

After 3-4 hours, 200 μL from each plate was sampled into a shallow-well plate and centrifuged at 4000 rpm for 6 min. The supernatant was removed and 225 μL of phosphate-buffered saline (PBS) was added to each well. Each plate was centrifuged again and the supernatant was removed. After a second PBS wash, 200 μL of PBS supplemented with 5 mM coumarin, 0.4% glycerol, and 50 μM ferric citrate was added to each well. The plates were centrifuged again, covered to prevent evaporation, and placed at 37° C. for 16 hours. Then, each plate was measured for fluorescence by excitation at 360 nm and emission at 460 nm.

Using the fluorescence readings, improved clones were identified by the following method. For each plate, the fluorescence in each well was normalized by the average value of the fluorescence in all the control wells (containing BZ85). Clones that demonstrated significant increases in fluorescence relative to the control were selected for a second fluorescence screen to confirm the improved enzyme activity. From this set, any clone that was above a desirable threshold was sequenced to identify the mutation that led to improved activity. Additional assays may also be performed to test other features of the enzyme.

A subset of the clones was selected for DNA sequencing to identify mutations that improve the activity of the enzyme. Table 1 shows the mutation(s) that was identified, along with the relative activity (activity normalized by controls) in the coumarin assay, the positions being numbered with respect to SEQ ID NO: 3.

TABLE 1

Mutations in the hydroxylase alpha subunit.

| Mutation(s) | Activity |
|---|---|
| L003P | 1.38 |
| L003P, L014P | 3.81 |
| L003P, L014P, L032P, F035L, R330T | 2.78 |
| L003P, L014P, S434N | 1.91 |
| A025S | 1.74 |
| Q026G | 1.20 |
| L032P, A262E | 1.24 |
| Q033K | 1.47 |
| Q033R | 1.17 |
| N042R, T044A | 1.25 |
| T044S | 1.21 |
| A053G | 1.28 |
| N054K | 1.49 |
| N054L | 1.86 |
| E055A | 1.30 |
| E055S, N375H | 1.11 |
| T056A | 1.37 |
| T056G | 1.72 |
| K057G | 1.15 |
| K057S | 1.33 |
| K057T | 1.11 |
| K061A | 2.25 |
| K061R | 1.98 |
| A130C | 2.49 |
| A130G, R419L | 2.01 |
| A130H | 1.78 |
| A130T | 1.66 |
| N135S | 1.24 |
| V154L | 1.80 |
| V154L, S263Q | 1.71 |
| G162C | 2.86 |
| Q163F | 1.26 |
| H168G | 1.43 |
| L216M | 1.12 |
| Y251M | 1.10 |
| Y251W | 1.24 |
| A264Q | 1.44 |
| T277G | 1.34 |
| I316S | 1.14 |
| G322N | 1.32 |
| Y347G | 1.32 |
| T356C | 1.91 |
| T356G | 2.27 |
| T356M | 1.60 |
| A374E | 1.41 |
| D381R | 1.56 |
| D381S | 2.38 |
| Y387I | 1.57 |
| Y387L | 2.05 |
| R393C | 1.33 |
| S399D | 1.11 |
| L405G | 1.63 |
| R419S | 1.53 |
| V420C | 1.43 |
| Q422E, K431E, E480G, D504E | 1.27 |
| K431E | 1.34 |
| G432A | 1.84 |
| A433G, A525Q | 1.32 |
| A433Q | 1.48 |
| A433T | 1.40 |

TABLE 1-continued

Mutations in the hydroxylase alpha subunit.

| Mutation(s) | Activity |
|---|---|
| S434G, K505E | 1.22 |
| S434N | 1.61 |
| Q444E | 1.31 |
| G453V | 2.07 |
| M456V | 1.44 |
| A459E, K513T | 1.27 |
| I469V | 1.50 |
| F470I, G475* | 1.43 |
| L485E | 1.43 |
| K493E | 1.41 |
| K493V | 1.30 |
| K505E | 1.28 |
| D510E | 1.23 |
| K513R | 1.25 |
| K513T | 1.16 |
| L515G | 1.89 |
| F526C | 1.33 |
| F526G | 1.27 |
| F526L | 1.33 |
| F526S | 1.46 |

The following describes the method for culturing the strains and measuring the bioconversion of methane to methanol. All strains were inoculated in 1 mL LB Miller supplemented with spectinomycin (100 µg/mL) and grown at 37° C. for 18 hours with shaking at 280 rpm. The cultures grew to stationary phase and 0.1 mL of these cultures was then used to inoculate two flasks containing sterile 10 mL LB supplemented with spectinomycin (100 µg/mL), arabinose (1 mM), L-cysteine (200 µM), and ferric citrate (50 µM). The cultures were grown with shaking at 37° C. until OD600~1.2 (approximately 4.0-4.5 hours). The cells were spun for 5 minutes at 4000 rpm, and re-suspended in 10 mL phosphate buffer solution (PBS). This 10 mL was split equally into two glass serum bottles, 5 mL in each. The bottles were then sealed with butyl rubber stoppers. A volume of 60 mL of either methane or air was measured into syringes and injected through the stopper and into each of the two bottles. The bottles were shaken at 37° C. for 16-25 hours, at which point the supernatant was sampled in order to measure methanol concentration.

Methanol was measured using a colorimetric assay (Cell Biolabs catalog number STA-620). Briefly, it measures methanol using an enzymatic reaction that produces hydrogen peroxide, which reacts with a colorimetric probe. 90 µL of a reaction mixture was combined with 10 µL of sample and incubated at 37° C. for 30 minutes. The composition of the assay mixture is described in Table 2. The absorbance at 570 nm was compared to a methanol standard curve, and methanol in each sample was quantified.

TABLE 2

Composition of the reaction mixture for the methanol assay.

| Component | Amount |
|---|---|
| Deionized water (mL) | 2.175 |
| 10x assay buffer (mL) | 0.25 |
| 100x Enzyme mixture (µL) | 25 |
| 50x colorimetric probe (µL) | 50 |
| Total reaction volume (mL) | 2.5 |

After raw absorbance data was collected, the data were processed as follows: background absorbance (media only) was subtracted from all samples, including the calibration samples. Each strain had been tested either with air injected or with methane injected. The absorbance from the air-injected sample was subtracted from the absorbance from the methane-injected sample. This absorbance value was compared with the calibration curve to determine the amount of methanol.

Some of the clones that were isolated by screening with the coumarin assay described above were subsequently selected for the methanol assay. Alongside these clones, a WT strain was assayed as a control. For each strain, the methanol titer was normalized by the OD600 (as a measure of the cell density) to measure the cellular productivity (methanol per cell). The data shown below in Table 3 has been normalized by this WT strain in order to show the improvements in methanol productivity, relative to the WT control as the starting point. Positions are numbered with respect to SEQ ID NO: 3.

TABLE 3

Improved mutants discovered by screening with methane as a substrate and measuring the methanol titers per OD600 relative to the WT mmoX gene.

| Mutation | Incubation Time (hours) | Titer/OD (normalized to WT) |
|---|---|---|
| G162C | 24.75 | 1.67 |
| R330T | 24.75 | 1.30 |

Example 2

Mutagenesis of the Mutant Accessory Protein B

The method described above (in Example 1) was applied in an identical fashion to the mutagenesis of the mmoB gene in pBZ34 (SEQ ID NO: 1), with the exception of the saturation mutagenesis primers being targeted to the mmoB gene instead of the mmoX gene. Screening with coumarin as the substrate or methane as the substrate was performed as described above.

Results are shown below in tables 4-5, wherein positions are numbered with respect to SEQ ID NO: 6.

TABLE 4

Mutations in accessory protein B with improved activity.

| Mutation(s) | Activity |
|---|---|
| V003G | 1.31 |
| L015M | 1.30 |
| K016G | 1.25 |
| V038G | 1.25 |
| T058E, T118E | 1.24 |
| N069K | 1.27 |
| A081G | 3.31 |
| N101G | 1.27 |
| V102A | 1.31 |
| V102L | 1.32 |
| Y103H | 2.02 |
| L106V | 1.27 |
| S110A | 1.40 |
| T112G | 1.50 |
| T112V | 1.30 |
| A116S | 1.54 |
| A116T | 1.49 |
| T118G | 1.34 |
| L119E | 1.26 |
| G120A | 1.83 |

TABLE 4-continued

| Mutations in accessory protein B with improved activity. | |
|---|---|
| Mutation(s) | Activity |
| G120E | 1.58 |
| T124C | 1.31 |
| T124G | 1.37 |
| T126S | 1.44 |
| M130D | 1.25 |
| M130V | 1.44 |
| G131S | 1.39 |
| R134A | 1.53 |
| R134G | 1.38 |
| R134W | 1.37 |
| L136A | 1.21 |
| D138S | 1.29 |
| Y139G | 1.28 |
| Y139S | 1.30 |
| Y139V | 1.28 |

TABLE 5

Improved mutants discovered by screening with methane as a substrate and measuring the methanol titers per OD600 relative to the WT mmoB gene.

| Mutation | Incubation Time (hours) | Titer/OD (normalized to WT) |
|---|---|---|
| G120E | 18.50 | 1.07 |

Example 3

Mutagenesis of Mutant Reductase Subunit C

The method described above (in Example 1) was applied in an identical fashion to the mutagenesis of the mmoC gene in pBZ34 (SEQ ID NO: 1), with the exception of the saturation mutagenesis primers being targeted to the mmoC gene instead of the mmoX gene.

Results are shown below in tables 6-7, wherein positions are numbered with respect to SEQ ID NO: 7.

TABLE 6

| Mutations in reductase subunit C with improved activity. | |
|---|---|
| Mutations | Activity |
| L017R, W240E | 2.71 |
| L017Q | 1.79 |
| I028G | 1.19 |
| L038G | 1.23 |
| E044R | 1.60 |
| E044G | 1.23 |
| G045R, S329G | 1.16 |
| T049L | 1.99 |
| D058K | 1.19 |
| K062L | 1.70 |
| C064Q | 1.17 |
| C064A, R330W | 1.15 |
| L069A | 1.30 |
| E074R | 1.41 |
| K087L, Q236M | 1.67 |
| L090Q, A216V | 1.17 |
| T097V | 1.17 |
| H098G | 1.41 |
| R100G, E288V | 1.11 |
| E110R, N308V | 1.31 |
| A111V | 1.21 |

TABLE 6-continued

| Mutations in reductase subunit C with improved activity. | |
|---|---|
| Mutations | Activity |
| L116V, K211V | 1.27 |
| V119C | 1.10 |
| Q125L | 1.30 |
| D133V, D286T | 1.35 |
| C135T | 1.55 |
| R138Q, F208Q | 1.16 |
| E143K, P144C | 1.67 |
| I152S | 1.17 |
| P153H | 1.37 |
| T155A, C279S | 1.14 |
| V157R | 1.12 |
| E174A | 1.14 |
| L180S | 1.43 |
| R184G | 1.16 |
| N191D | 1.85 |
| G196V | 1.22 |
| P204S | 1.15 |
| G209W | 1.23 |
| R213G, W281R | 1.50 |
| A222G | 1.13 |
| R235G | 1.13 |
| Q238G | 1.14 |
| A242V | 1.57 |
| P243G, E245D | 1.12 |
| N244G | 1.14 |
| E245M | 1.68 |
| T246M | 1.12 |
| C324G | 1.39 |

TABLE 7

Improved mutants discovered by screening with methane as a substrate and measuring the methanol titers per OD600 relative to the WT mmoC gene.

| Mutation | Incubation Time (hours) | Titer/OD (normalized to WT) |
|---|---|---|
| Q125L | 21 | 1.81 |
| E174A | 21 | 1.75 |
| N168A | 21 | 1.74 |
| V140W | 16 | 1.25 |
| N308G | 16 | 1.19 |

Example 4

Mutagenesis of the Hydroxylase Beta Subunit

The method described above (in Example 1) was applied in an identical fashion to the mutagenesis of the mmoY gene in pNH265 (SEQ ID NO: 2), with the exception of the saturation mutagenesis primers being targeted to the mmoY gene instead of the mmoX gene.

Results are shown below in tables 8-9, wherein positions are numbered with respect to SEQ ID NO: 4.

TABLE 8

| Mutations in the hydroxylase beta subunit with improved activity. | |
|---|---|
| Mutation(s) | Activity |
| N032V | 1.14 |
| G036L | 1.14 |
| L046V | 1.14 |
| T047H, | 1.10 |

TABLE 8-continued

| Mutations in the hydroxylase beta subunit with improved activity. | |
|---|---|
| Mutation(s) | Activity |
| A151G | |
| T047V | 1.14 |
| P058N | 1.28 |
| A064G | 1.26 |
| T087V | 1.12 |
| V093G | 1.11 |
| Y109A | 1.14 |
| Y109E | 1.17 |
| Y109F | 1.11 |
| Y109V | 1.17 |
| I133S | 1.41 |
| E143T | 1.17 |
| N146R | 1.28 |
| N155G | 1.30 |
| Y157W | 1.31 |
| F160K | 1.15 |
| F160M | 1.21 |
| F160T | 1.40 |
| F160V | 1.35 |
| A162T, K202Q | 1.42 |
| A167Q | 1.25 |
| W182M | 1.12 |
| G183A | 1.31 |
| G183S | 1.18 |
| F184S | 1.14 |
| K186N | 1.28 |
| A201G, G233R | 1.29 |
| K202A | 1.55 |
| K202R, A230G | 1.24 |
| K202S | 1.43 |
| I203V, G273T | 1.62 |
| V204S | 1.27 |
| G206E | 1.50 |
| D208A, R318I | 1.33 |
| E209R | 2.33 |
| T211I | 1.37 |
| A212G, A330R | 1.32 |
| A212G | 2.79 |
| V213G | 1.48 |
| V213W | 1.26 |
| P214V | 1.29 |
| A216G, G273V | 1.53 |
| E217L | 1.30 |
| N220V | 1.77 |
| E222R, D305L | 1.36 |
| Y224M | 1.34 |
| K225G, R333V | 1.99 |
| S226G | 1.53 |
| G233L | 1.34 |
| G233W | 1.84 |
| Q236G | 1.61 |
| Q236V | 1.38 |
| Q236W | 1.48 |
| F239L | 1.60 |
| N242G | 1.29 |
| N242P, A291T | 1.76 |
| N242V | 1.48 |
| S244G, I281G | 1.35 |
| A250C, L325G | 1.31 |
| F256W | 1.25 |
| V260C | 1.44 |
| Q266V | 1.49 |
| A269G | 1.35 |
| P270R, D306Q | 1.35 |
| F272K | 1.24 |
| L276V | 1.54 |
| L303G | 2.58 |
| G304A | 1.22 |
| D305A | 1.38 |
| D305G | 1.58 |
| D305R | 1.74 |
| D305W | 1.62 |
| D306E | 1.61 |
| D306R | 1.66 |
| E308G, R314H | 1.22 |
| S310R | 1.66 |
| S310W | 1.75 |
| D311A | 1.39 |
| D311G | 1.83 |
| R314G | 1.26 |
| R314Q | 1.30 |
| R318G | 1.34 |
| G322R | 1.45 |
| T328G | 1.44 |
| I329W | 2.79 |
| F335G | 1.61 |
| M336G | 1.34 |
| L356G | 1.58 |
| I364G | 1.39 |
| D372W | 1.44 |

TABLE 9

| Improved mutants discovered by screening with methane as a substrate and measuring the methanol titers per OD600 relative to the WT mmoY gene. | | |
|---|---|---|
| Mutation | Incubation Time (hours) | Methanol Titer/OD (normalized to WT) |
| N146R | 18 | 1.56 |
| G233W | 18 | 1.15 |
| D305R | 18 | 1.18 |
| A212G | 18 | 1.39 |
| R314G | 18.75 | 1.15 |
| I329W | 18 | 1.49 |

Example 5

Mutagenesis of Hydroxylase Gamma Subunit

The method described above (in Example 1) was applied in an identical fashion to the mutagenesis of the mmoZ gene in pNH265 (SEQ ID NO: 2), with the exception of the saturation mutagenesis primers being targeted to the mmoZ gene instead of the mmoX gene.

Results are shown below in tables 10 and 11, wherein positions are numbered with respect to SEQ ID NO: 5.

TABLE 10

| Mutations in hydroxylase gamma subunit with improved activity (measured as fold-improvement over unmutagenized sequence). | |
|---|---|
| Mutation(s) | Activity |
| D010R | 1.21 |
| D010V | 1.60 |
| N017F | 1.13 |
| N017W | 1.41 |
| K018A | 1.10 |
| K018E | 1.38 |
| A020G | 1.22 |
| Q021H, I112V | 1.38 |

TABLE 10-continued

Mutations in hydroxylase gamma subunit with improved activity (measured as fold-improvement over unmutagenized sequence).

| Mutation(s) | Activity |
|---|---|
| N023A | 1.11 |
| N023D | 1.11 |
| N023E | 1.32 |
| N023G | 1.35 |
| N023L | 1.21 |
| N023L, A117L | 1.54 |
| N023V | 1.22 |
| T024E | 1.24 |
| T024V, F043K | 1.42 |
| K027G | 1.33 |
| K027Q | 1.30 |
| K027R | 1.49 |
| A029G | 1.13 |
| A029G, E154G | 1.35 |
| M031W | 1.43 |
| K033V | 1.18 |
| Q034A | 1.19 |
| Q034K | 1.34 |
| T041G | 1.15 |
| F043S | 1.10 |
| F043V | 1.26 |
| N045G | 1.14 |
| S046G | 1.18 |
| S046I | 1.12 |
| Y047S | 1.37 |
| Y047T | 1.29 |
| D050G | 1.63 |
| N051G | 1.72 |
| N051V | 1.14 |
| D052G | 1.81 |
| Y053C | 1.66 |
| I056L | 1.31 |
| K063G | 1.23 |
| K063T | 1.13 |
| V066D | 1.33 |
| L067E | 1.31 |
| R070E | 1.77 |
| R070G | 1.11 |
| R070V | 1.34 |
| H079E | 1.28 |
| K080M | 1.27 |
| D103G, L166E | 1.15 |
| Q116S | 1.25 |
| Y127F | 1.29 |
| L129G | 1.18 |
| G136Q | 1.64 |
| G136S | 1.24 |
| N144D | 1.22 |
| N144G | 1.50 |
| N144V | 1.24 |
| Y147D | 1.30 |
| E153G | 1.46 |
| E154G | 1.42 |
| R156A | 1.13 |
| H165G | 1.40 |
| L166G | 1.29 |

TABLE 11

Improved mutants discovered by screening with methane as a substrate and measuring the methanol titers per OD600 relative to the Wild-type mmoZ gene.

| Mutation | Incubation Time (hours) | Methanol Titer/OD (normalized to WT) |
|---|---|---|
| H165G | 20.25 | 1.07 |
| Y47S | 20.25 | 1.12 |
| Y47T | 18.75 | 1.35 |
| K27R | 18.75 | 1.20 |
| M31W | 18.75 | 1.23 |

TABLE 11-continued

Improved mutants discovered by screening with methane as a substrate and measuring the methanol titers per OD600 relative to the Wild-type mmoZ gene.

| Mutation | Incubation Time (hours) | Methanol Titer/OD (normalized to WT) |
|---|---|---|
| G136Q | 18.75 | 1.41 |
| A29G, E154G | 18.75 | 1.40 |

Example 6

Mutagenesis of mmoD

The method described above (in Example 1) was applied in an identical fashion to the mutagenesis of the mmoD gene in pNH265 (SEQ ID NO: 2), with the exception of the saturation mutagenesis primers being targeted to the mmoD gene instead of the mmoX gene.

Results are shown below in tables 12 and 13, wherein positions are numbered with respect to SEQ ID NO: 8.

TABLE 12

Mutations in MMOD. mmoD mutants

| Mutation | Normalized Titer Improvement |
|---|---|
| S4R | 1.17 |
| A5S | 1.16 |
| Q7G | 1.49 |
| P8G | 1.12 |
| F9G | 1.20 |
| S10R | 1.11 |
| A13E | 1.24 |
| D14R | 1.20 |
| F17G | 1.25 |
| E18R | 1.30 |
| P20G | 1.22 |
| R21L | 1.23 |
| P22R | 2.10 |
| A24G | 1.12 |
| F27V | 1.90 |
| T40R | 1.27 |
| E60Q | 2.70 |
| S74A | 1.15 |
| T79G | 1.39 |
| T79S | 1.71 |
| H80G | 1.25 |
| E89D | 1.39 |
| Q90S | 1.24 |
| A92P | 1.26 |
| P93A | 1.36 |
| D96R | 1.17 |

TABLE 13

Improved mutants discovered by screening with methane as a substrate and measuring the methanol titers per OD600 relative to the WT mmoD gene.

| Mutation | Incubation Time (hours) | Methanol Titer/OD (normalized to WT) |
|---|---|---|
| E60Q | 18.5 | 1.47 |

Example 7

Mutagenesis of groEL-2

The method described above (in Example 1) was applied in an identical fashion to the mutagenesis of the groEL-2 gene in pNH265 (SEQ ID NO: 2), with the exception of the saturation mutagenesis primers being targeted to the groEL-2 gene instead of the mmoX gene.

Results are shown below in tables 14 and 15, wherein positions are numbered with respect to SEQ ID NO: 9.

TABLE 14

Mutations in groEL-2.
groEL-2 mutations

| Mutation | Normalized Titer Improvement |
|---|---|
| A109E | 1.43 |
| A109P | 1.94 |
| G160A | 1.75 |
| D168V | 1.39 |
| A169S | 2.50 |
| G171P | 1.05 |
| Q182W | 2.12 |
| L187V | 1.31 |
| T396L | 1.33 |
| V405G | 1.27 |
| V405D | 1.31 |
| N409G | 2.64 |
| A438K | 1.20 |
| D444S | 1.11 |
| P461V | 1.42 |
| G466L | 1.12 |
| A478L | 1.13 |
| A478R | 1.14 |
| A484E | 1.11 |
| A484G | 1.06 |
| N485T | 1.17 |
| G495H | 1.15 |
| V522L | 1.31 |
| G524T | 1.16 |
| T529G | 1.42 |

TABLE 15

Improved mutants discovered by screening with methane as a substrate and measuring the methanol titers per OD600 relative to the WT groEL-2 gene.

| Mutation | Incubation Time (hours) | Methanol Titer/OD (normalized to WT) |
|---|---|---|
| N409G | 18.5 | 1.52 |

All publications and patent applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof.

The invention claimed is:

1. A mutant soluble diiron monooxygenase system, comprising a mutant protein folding chaperone groEL-2 comprising an amino acid sequence having at least 80% identity to SEQ ID NO: 9, wherein the mutant protein folding chaperone groEL-2 comprises a mutation at residue position 409, wherein the residue position is numbered with respect to SEQ ID NO: 9.

2. The mutant soluble diiron monooxygenase system of claim 1, wherein the mutation is a substitution N409G, wherein the residue position is numbered with respect to SEQ ID NO: 9.

3. One or more isolated nucleic acids encoding one or more polypeptides comprising the mutant soluble diiron monooxygenase system of claim 1.

4. One or more vectors comprising the one or more isolated nucleic acids of claim 3.

5. One or more host cells comprising the one or more vectors of claim 4.

6. The one or more host cells of claim 5, wherein the one or more host cells comprises a prokaryotic cell.

7. The one or more host cells of claim 6, wherein the prokaryotic cell is *Escherichia coli, Corynebacterium glutamicum*, or *Bacillus methanolicus*.

* * * * *

SEQUENCE LISTING

```
<160> NUMBER OF SEQ ID NOS: 9

<210> SEQ ID NO 1
<211> LENGTH: 13237
<212> TYPE: DNA
<213> ORGANISM: Methylococcus capsulatus str. Bath
<220> FEATURE:
<221> NAME/KEY: misc_feature
<222> LOCATION: (1)..(13237)
<223> OTHER INFORMATION: pBZ34

<400> SEQUENCE: 1

ggcgggcgct gcggacacat acaaagttac ccacagattc cgtggataag caggggacta      60

acatgtgagg caaaacagca gggccgcgcc ggtggcgttt ttccataggc tccgccctcc     120

tgccagagtt cacataaaca gacgcttttc cggtgcatct gtgggagccg tgaggctcaa     180

ccatgaatct gacagtacgg gcgaaacccg acaggactta aagatcccca ccgtttccgg     240

cgggtcgctc cctcttgcgc tctcctgttc cgaccctgcc gtttaccgga tacctgttcc     300

gcctttctcc cttacgggaa gtgtggcgct ttctcatagc tcacacactg gtatctcggc     360

tcggtgtagg tcgttcgctc caagctgggc tgtaagcaag aactccccgt tcagcccgac     420

tgctgcgcct tatccggtaa ctgttcactt gagtccaacc cggaaaagca cggtaaaacg     480

ccactggcag cagccattgg taactgggag ttcgcagagg atttgtttag ctaaacacgc     540

ggttgctctt gaagtgtgcg ccaaagtccg gctacactgg aaggacagat ttggttgctg     600

tgctctgcga aagccagtta ccacggttaa gcagttcccc aactgactta accttcgatc     660
```

```
aaaccacctc cccaggtggt tttttcgttt acagggcaaa agattacgcg cagaaaaaaa    720
ggatctcaag aagatccttt gatcttttct actgaaccgc tctagatttc agtgcaattt    780
atctcttcaa atgtagcacc tgaagtcagc cccatacgat ataagttgta attctcatgt    840
tagtcatgcc ccgcgcccac cggaaggagc tgactgggtt gaaggctctc aagggcatcg    900
gtcgagatcc cggtgcctaa tgagtgagct aacttttgac ggctagctca gtcctaggga    960
taatgctagc accagcctcg agggaaacca cgtaagctcc ggcgtttaaa cacccataac   1020
agatacggac tttctcaaag gagagttatc agtgaaaatc cgcccgttac atgaccgtgt   1080
catcatcaaa cgcttggaag aagagcgtac ctcggcgggc gggattgtca ttccagatag   1140
cgcagctgaa aaaccgatgc gtggtgaaat cctggcagtg ggcaatggaa aagtgcttga   1200
taatggagag gtacgtgctt tacaggtgaa agtgggtgat aaagtgctct ttgggaaata   1260
cgcgggtacg gaggttaaag tagatgggga agatgttgtt gtcatgcgtg aagatgacat   1320
tctggctgtg ttagaatctt aatccgcgca cgacactgaa catacgaatt taaggaataa   1380
agataatggc gaaagaagtt gtgtatcgtg gtagtgcgcg ccagcgtatg atgcagggta   1440
ttgaaattct cgctcgcgcc gctattccaa cgctgggggc aaccggcccg agcgtcatga   1500
ttcaacatcg cgccgatggt ctgccaccca tttctacacg cgatggcgtt accgtagcga   1560
attctattgt tttaaaagac cgtgtcgcga acctgggtgc ccgcctgctg cgcgacgtag   1620
ccggtacaat gagccgtgaa gccggcgacg gcacgacgac tgcgatcgta ttggcccgcc   1680
acatcgcccg tgagatgttt aaatcgctgg ccgtgggtgc agatccgatc gcgctgaaac   1740
gtggtatcga tcgcgccgtt gctcgtgtgt ccgaagatat tggggcgcgt gcgtggcgtg   1800
gcgataaaga aagcgtgatc ctgggtgtcg ctgctgtggc gacgaaaggc gaaccgggcg   1860
ttggccgtct gctgctggag gctctcgatg cagtgggtgt tcacggtgcc gtttctatcg   1920
aactgggcca acgtcgtgaa gatctgctgg acgtcgtcga tggctatcgc tgggaaaaag   1980
gttatttatc tccctacttt gtcacggacc gtgcccgcga actcgcggaa ctggaggatg   2040
tctacctgct catgaccgac cgcgaagtgg ttgacttcat cgaccttgta cctctgctgg   2100
aggccgtgac ggaagcagga ggctccctgc tgattgccgc ggatcgtgtg cacgaaaagg   2160
ccttagcggg gctgcttctg aatcacgtgc gcggtgtctt caaggccgtg gccgtaaccg   2220
ctccgggttt tggcgacaaa cgcccgaacc gtttacttga cctggccgcg ttaaccggcg   2280
gtcgtgccgt gctcgaagct caaggcgacc gtctggaccg tgttaccctc gcggatctgg   2340
gccgtgtgcg ccgtgccgtg gtgtcggcag atgataccgc gctgcttggc atcccgggca   2400
ccgaagctag ccgtgcacgc ctcgaaggtc tgcgtttaga agcagagcag taccgtgcgc   2460
tgaaaccagg gcagggttct gccaccgggc gcctgcacga acttgaagaa attgaagcgc   2520
gcattgtggg tctgtccgga aagagcgccg tttatcgcgt cggaggtgtg accgatgtgg   2580
aaatgaaaga gcgcatggtt cgcatcgaaa acgcttaccg ttcggtggta agtgcgctgg   2640
aggaaggcgt gctccctggc ggtggtgtcg gctttctggg tagtatgccg gtgcttgcgg   2700
aattggaggc ccgcgacgca gatgaagctc gcgggattgg gattgtacgc agcgccttaa   2760
cggagcctct tcgtattatc ggcgaaaata gtggcttgag cggtgaagcc gttgttgcca   2820
aagtcatgga tcatgccaac ccgggatggg gttacgacca ggagtctggc tctttttgcg   2880
acctgcatgc gcgtgggatc tgggatgctg ctaaagtgtt acgtctcgcg ttggagaagg   2940
cagcctctgt tgctgggacc tttctgacaa ccgaagctgt tgttctcgaa attccggata   3000
```

-continued

```
cagatgcgtt cgcagggttc agtgcagaat gggctgccgc cacgcgcgaa gatccgcgcg   3060
tatgagttta aacgcggccg caatttgaac gcacccataa cagatacgga ctttctcaaa   3120
ggagagttat caatgaatat tcgtccattg catgatcgcg tgatcgtcaa gcgtaaagaa   3180
gttgaaacta aatctgctgg cggcatcgtt ctgaccggct ctgcagcggc taaatccacc   3240
cgcggcgaag tgctggctgt cggcaatggc cgtatccttg aaaatggcga agtgaagccg   3300
ctggatgtga aagttggcga catcgttatt ttcaacgatg gctacggtgt gaaatctgag   3360
aagatcgaca atgaagaagt gttgatcatg tccgaaagcg acattctggc aattgttgaa   3420
gcgtaatccg cgcacgacac tgaacatacg aatttaagga ataaagataa tggcagctaa   3480
agacgtaaaa ttcggtaacg acgctcgtgt gaaaatgctg cgcggcgtaa acgtactggc   3540
agatgcagtg aaagttaccc tcggtccaaa aggccgtaac gtagttctgg ataaatcttt   3600
cggtgcaccg accatcacca aagatggtgt ttccgttgct cgtgaaatcg aactggaaga   3660
caagttcgaa aatatgggtg cgcagatggt gaaagaagtt gcctctaaag caaacgacgc   3720
tgcaggcgac ggtaccacca ctgcaaccgt actggctcag gctatcatca ctgaaggtct   3780
gaaagctgtt gctgcgggca tgaacccgat ggacctgaaa cgtggtatcg acaaagcggt   3840
taccgctgca gttgaagaac tgaaagcgct gtccgtacca tgctctgact ctaaagcgat   3900
tgctcaggtt ggtaccatct ccgctaactc cgacgaaacc gtaggtaaac tgatcgctga   3960
agcgatggac aaagtcggta aagaaggcgt tatcaccgtt gaagacggta ccggtctgca   4020
ggacgaactg gacgtggttg aaggtatgca gttcgaccgt ggctacctgt ctccttactt   4080
catcaacaag ccggaaactg gcgcagtaga actggaaagc ccgttcatcc tgctggctga   4140
caagaaaatc tccaacatcc gcgaaatgct gccggttctg gaagctgttg ccaaagcagg   4200
caaaccgctg ctgatcatcg ctgaagatgt agaaggcgaa gcgctggcaa ctctggttgt   4260
taacaccatg cgtggcatcg tgaaagtcgc tgcggttaaa gcaccgggct tcggcgatcg   4320
tcgtaaagct atgctgcagg atatcgcaac cctgactggc ggtaccgtga tctctgaaga   4380
gatcggtatg gagctggaaa aagcaaccct ggaagacctg ggtcaggcta aacgtgttgt   4440
gatcaacaaa gacaccacca ctatcatcga tggcgtgggt gaagaagctg caatccaggg   4500
ccgtgttgct cagatccgtc agcagattga agaagcaact tctgactacg accgtgaaaa   4560
actgcaggaa cgcgtagcga aactggcagg cggcgttgca gttatcaaag tgggtgctgc   4620
taccgaagtt gaaatgaaag agaaaaaagc acgcgttgaa gatgccctgc acgcgacccg   4680
tgctgcggta gaagaaggcg tggttgctgg tggtggtgtt gcgctgatcc gcgtagcgtc   4740
taaactggct gacctgcgtg gtcagaacga agaccagaac gtgggtatca aagttgcact   4800
gcgtgcaatg gaagctccgc tgcgtcagat cgtattgaac tgcggcgaag aaccgtctgt   4860
tgttgctaac accgttaaag gcggcgacgg caactacggt tacaacgcag caaccgaaga   4920
atacggcaac atgatcgaca tgggtatcct ggatccaacc aaagtaactc gttctgctct   4980
gcagtacgca gcttctgtgg ctggcctgat gatcaccacc gaatgcatgg ttaccgacct   5040
gccgaaaaac gatgcagctg acttaggcgc tgctggcggt atgggcggca tgatgtaagt   5100
ttaaacgcgg ccgcaatttg aacgccagca catggactct cgagtctact agcgcagctt   5160
aattaaccta ggctgctgcc accgctgagc aataactagc ataacccctt ggggcctcta   5220
aacgggtctt gaggggtttt ttgctgaaac ctcaggcatt tgagaagcac acggtcacac   5280
tgcttccggt agtcaataaa ccggtaaacc agcaatagac ataagcggtg cataatgtgc   5340
ctgtcaaatg gacgaagcag ggattctgca aaccctatgc tactccgtca agccgtcaat   5400
```

```
tgtctgattc gttaccaatt atgacaactt gacggctaca tcattcactt tttcttcaca   5460
accggcacgg aactcgctcg ggctggcccc ggtgcatttt ttaaataccc gcgagaaata   5520
gagttgatcg tcaaaaccaa cattgcgacc gacggtggcg ataggcatcc gggtggtgct   5580
caaaagcagc ttcgcctggc tgatacgttg gtcctcgcgc cagcttaaga cgctaatccc   5640
taactgctgg cggaaaagat gtgacagacg cgacggcgac aagcaaacat gctgtgcgac   5700
gctggcgata tcaaaattgc tgtctgccag gtgatcgctg atgtactgac aagcctcgcg   5760
tacccgatta tccatcggtg gatggagcga ctcgttaatc gcttccatgc gccgcagtaa   5820
caattgctca agcagattta tcgccagcag ctccgaatag cgcccttccc cttgcccggc   5880
gttaatgatt tgcccaaaca ggtcgctgaa atgcggctgg tgcgcttcat ccgggcgaaa   5940
gaaccccgta ttggcaaata ttgacggcca gttaagccat tcatgccagt aggcgcgcgg   6000
acgaaagtaa acccactggt gataccattc gcgagcctcc ggatgacgac cgtagtgatg   6060
aatctctcct ggcgggaaca gcaaaatatc acccggtcgg caaacaaatt ctcgtccctg   6120
atttttcacc accccctgac cgcgaatggt gagattgaga atataacctt tcattcccag   6180
cggtcggtcg ataaaaaaat cgagataacc gttggcctca atcggcgtta aacccgccac   6240
cagatgggca ttaaacgagt atcccggcag caggggatca ttttgcgctt cagccatact   6300
tttcatactc ccgccattca gagaagaaac caattgtcca tattgcatca gacattgccg   6360
tcactgcgtc ttttactggc tcttctcgct aaccaaaccg gtaaccccgc ttattaaaag   6420
cattctgtaa caaagcggga ccaaagccat gacaaaaacg cgtaacaaaa gtgtctataa   6480
tcacggcaga aaagtccaca ttgattattt gcacggcgtc acactttgct atgccatagc   6540
atttttatcc ataagattag cggatcctac ctgacgcttt ttatcgcaac tctggacaat   6600
gtctccatac ccgttttttt gggcgacctc gtcggaggtt gtatgtccgg tgttccgtga   6660
cgtcatcggg cattcatcat tcatagaatg tgttacggag gaaacaagta atggcactta   6720
gcaccgcaac caaggccgcg acggacgcgc tggctgccaa tcgggcaccc accagcgtga   6780
atgcacagga agtgcaccgt tggctccaga gcttcaactg ggatttcaag aacaaccgga   6840
ccaagtacgc caccaagtac aagatggcga acgagaccaa ggaacagttc aagctgatcg   6900
ccaaggaata tgcgcgcatg gaggcagtca aggacgaaag gcagttcggt agcctgcagg   6960
atgcgctgac ccgcctcaac gccggtgttc gcgttcatcc gaagtggaac gagaccatga   7020
aagtggtttc gaacttcctg gaagtgggcg aatacaacgc catcgccgct accgggatgc   7080
tgtgggattc cgcccaggcg gcggaacaga agaacggcta tctggcccag gtgttggatg   7140
aaatccgcca cacccaccag tgtgcctacg tcaactacta cttcgcgaag aacggccagg   7200
acccggccgg tcacaacgat gctcgccgca cccgtaccat cggtccgctg tggaagggca   7260
tgaagcgcgt gttttccgac ggcttcattt ccggcgacgc cgtggaatgc tccctcaacc   7320
tgcagctggt gggtgaggcc tgcttcacca atccgctgat cgtcgcagtg accgaatggg   7380
ctgccgccaa cggcgatgaa atcaccccga cggtgttcct gtcgatcgag accgacgaac   7440
tgcgccacat ggccaacggt taccagaccg tcgtttccat cgccaacgat ccggcttccg   7500
ccaagtatct caacacggac ctgaacaacg ccttctggac ccagcagaag tacttcacgc   7560
cggtgttggg catgctgttc gagtatggct ccaagttcaa ggtcgagccg tgggtcaaga   7620
cgtggaaccg ctgggtgtac gaggactggg gcggcatctg gatcggccgt ctgggcaagt   7680
acggggtgga gtcgccgcgc agcctcaagg acgccaagca ggacgcttac tgggctcacc   7740
```

-continued

```
acgacctgta tctgctggct tatgcgctgt ggccgaccgg cttcttccgt ctggcgctgc   7800
cggatcagga agaaatggag tggttcgagg ccaactaccc cggctggtac gaccactacg   7860
gcaagatcta cgaggaatgg cgcgcccgcg gttgcgagga tccgtcctcg ggcttcatcc   7920
cgctgatgtg gttcatcgaa aacaaccatc ccatctacat cgatcgcgtg tcgcaagtgc   7980
cgttctgccc gagcttggcc aagggcgcca gcaccctgcg cgtgcacgag tacaacggcc   8040
agatgcacac cttcagcgac cagtggggcg agcgcatgtg gctggccgag ccggagcgct   8100
acgagtgcca gaacatcttc gaacagtacg aaggacgcga actgtcggaa gtgatcgccg   8160
aactgcacgg gctgcgcagt gatggcaaga ccctgatcgc ccagccgcat gtccgtggcg   8220
acaagctgtg gacgttggac gatatcaaac gcctgaactg cgtcttcaag aacccggtga   8280
aggcattcaa ttgaaacggg tgtcgggctc cgtcacaggg cggggcccga cgcacgatcg   8340
ttcgatcaac ctcaaaccaa aaaggaacat cgatatgagc atgttaggag aaagacgccg   8400
cggtctgacc gatccggaaa tggcggccgt cattttgaag gcgcttcctg aagctccgct   8460
ggacggcaac aacaagatgg gttatttcgt caccccccgc tggaaacgct tgacggaata   8520
tgaagccctg accgtttatg cgcagcccaa cgccgactgg atcgccggcg gcctggactg   8580
gggcgactgg acccagaaat tccacggcgg ccgcccttcc tggggcaacg agaccacgga   8640
gctgcgcacc gtcgactggt tcaagcaccg tgacccgctc cgccgttggc atgcgccgta   8700
cgtcaaggac aaggccgagg aatggcgcta caccgaccgc ttcctgcagg gttactccgc   8760
cgacggtcag atccgggcga tgaacccgac ctggcgggac gagttcatca accggtattg   8820
gggcgccttc ctgttcaacg aatacggatt gttcaacgct cattcgcagg gcgcccggga   8880
ggcgctgtcg gacgtaaccc gcgtcagcct ggctttctgg ggcttcgaca agatcgacat   8940
cgcccagatg atccaactcg aacggggttt cctcgccaag atcgtacccg gtttcgacga   9000
gtccacagcg gtgccgaagg ccgaatggac gaacggggag gtctacaaga gcgcccgtct   9060
ggccgtggaa gggctgtggc aggaggtgtt cgactggaac gagagcgctt tctcggtgca   9120
cgccgtctat gacgcgctgt tcggtcagtt cgtccgccgc gagttctttc agcggctggc   9180
tccccgcttc ggcgacaatc tgacgccatt cttcatcaac caggcccaga catacttcca   9240
gatcgccaag cagggcgtac aggatctgta ttacaactgt ctgggtgacg atccggagtt   9300
cagcgattac aaccgtaccg tgatgcgcaa ctggaccggc aagtggctgg agcccacgat   9360
cgccgctctg cgcgacttca tggggctgtt tgcgaagctg ccggcgggca ccactgacaa   9420
ggaagaaatc accgcgtccc tgtaccgggt ggtcgacgac tggatcgagg actacgccag   9480
caggatcgac ttcaaggcgg accgcgatca gatcgttaaa gcggttctgg caggattgaa   9540
ataatagagg aactattacg atgagcgtaa acagcaacgc atacgacgcc ggcatcatgg   9600
gcctgaaagg caaggacttc gccgatcagt tctttgccga cgaaaaccaa gtggtccatg   9660
aaagcgacac ggtcgttctg gtcctcaaga agtcggacga gatcaatacc tttatcgagg   9720
agatccttct gacggactac aagaagaacg tcaatccgac ggtaaacgtg gaagaccgcg   9780
cgggttactg gtggatcaag gccaacggca agatcgaggt cgattgcgac gagatttccg   9840
agctgttggg gcggcagttc aacgtctacg acttcctcgt cgacgtttcc tccaccatcg   9900
gccgggccta taccctgggc aacaagttca ccattaccag tgagctgatg ggcctggacc   9960
gcaagctcga agactatcac gcttaaggag aatgacatgg cgaaactggg tatacacagc  10020
aacgacaccc gcgacgcctg ggtgaacaag atcgcgcagc tcaacaccct ggaaaaagcg  10080
gccgagatgc tgaagcagtt ccggatggac cacaccacgc cgttccgcaa cagctacgaa  10140
```

```
ctggacaacg actacctctg gatcgaggcc aagctcgaag agaaggtcgc cgtcctcaag  10200
gcacgcgcct tcaacgaggt ggacttccgt cataagaccg ctttcggcga ggatgccaag  10260
tccgttctgg acggcaccgt cgcgaagatg aacgcggcca aggacaagtg ggaggcggag  10320
aagatccata tcggtttccg ccaggcctac aagccgccga tcatgccggt gaactatttc  10380
ctggacggcg agcgtcagtt ggggacccgg ctgatggaac tgcgcaacct caactactac  10440
gacacgccgc tggaagaact gcgcaaacag cgcggtgtgc gggtggtgca tctgcagtcg  10500
ccgcactgaa gggaggaagt ctcgccctgg acgcgacggc atcgccgtga agtccagggg  10560
gcagggatgc cgttccgggc cggcaggctg gcccggaatc tctggttttc agggggcgtg  10620
ccggtccacg gctccccccct ccatctttcg taaggaaatc accatggtcg aatcggcatt  10680
tcagccattt tcgggcgacg cagacgaatg gttcgaggaa ccacggcccc aggccggttt  10740
cttcccttcc gcggactggc atctgctcaa acgggacgag acctacgcag cctatgccaa  10800
ggatctcgat ttcatgtggc ggtgggtcat cgtccgggaa gaaaggatcg tccaggaggg  10860
ttgctcgatc agcctggagt cgtcgatccg cgccgtgacg cacgtactga attattttgg  10920
tatgaccgaa caacgcgccc cggcagagga ccggaccggc ggagttcaac attgaacagg  10980
taagtttatg cagcgagttc acactatcac ggcggtgacg gaggatggcg aatcgctccg  11040
cttcgaatgc cgttcggacg aggacgtcat caccgccgcc ctgcgccaga acatctttct  11100
gatgtcgtcc tgccgggagg gcggctgtgc gacctgcaag gccttgtgca gcgaaggga  11160
ctacgacctc aagggctgca gcgttcaggc gctgccgccg gaagaggagg aggaagggtt  11220
ggtgttgttg tgccggacct acccgaagac cgacctggaa atcgaactgc cctataccca  11280
ttgccgcatc agttttggtg aggtcggcag tttcgaggcg gaggtcgtcg gcctcaactg  11340
ggtttcgagc aacaccgtcc agtttctttt gcagaagcgg cccgacgagt gcggcaaccg  11400
tggcgtgaaa ttcgaacccg gtcagttcat ggacctgacc atccccggca ccgatgtctc  11460
ccgctcctac tcgccggcga accttcctaa tcccgaaggc cgcctggagt tcctgatccg  11520
cgtgttaccg gagggacggt tttcggacta cctgcgcaat gacgcgcgtg tcggacaggt  11580
cctctcggtc aaagggccac tgggcgtgtt cggtctcaag gagcggggca tggcgccgcg  11640
ctatttcgtg gccggcggca ccgggttggc gccggtggtc tcgatggtgc ggcagatgca  11700
ggagtggacc gcgccgaacg agacccgcat ctatttcggt gtgaacaccg agccggaatt  11760
gttctacatc gacgagctca aatccctgga acgatcgatg cgcaatctca ccgtgaaggc  11820
ctgtgtctgg cacccgagcg gggactggga aggcgagcag ggctcgccca tcgatgcgtt  11880
gcgggaagac ctggagtcct ccgacgccaa cccggacatt tatttgtgcg gtccgccggg  11940
catgatcgat gccgcctgcg agctggtacg cagccgcggt atccccggcg aacaggtctt  12000
cttcgaaaaa ttcctgccgt ccggggcggc ctgaaccggg gaagtaccgt gaccaccgag  12060
cagttcccgc cccaattcct gcgtgaaatg atcgagcagc tggacgccag catccaggag  12120
ctcgcacgca aggaaaaggg acttgcggca tccctgggca cgggccgggt cgccgagctc  12180
aaggaatact gggaccacgt tgttacaacc aattaaccaa ttctgactat ttaacgaccc  12240
tgccctgaac cgacgaccgg gtcatcgtgg ccggatcttg cggcccctcg gcttgaacga  12300
attgttagac attatttgcc gactaccttg gtgatctcgc ctttcacgta gtggacaaat  12360
tcttccaact gatctgcgcg cgaggccaag cgatcttctt cttgtccaag ataagcctgt  12420
ctagcttcaa gtatgacggg ctgatactgg gccggcaggc gctccattgc ccagtcggca  12480
```

```
gcgacatcct tcggcgcgat tttgccggtt actgcgctgt accaaatgcg ggacaacgta  12540

agcactacat ttcgctcatc gccagcccag tcgggcggcg agttccatag cgttaaggtt  12600

tcatttagcg cctcaaatag atcctgttca ggaaccggat caaagagttc ctccgccgct  12660

ggacctacca aggcaacgct atgttctctt gcttttgtca gcaagatagc cagatcaatg  12720

tcgatcgtgg ctggctcgaa gatacctgca agaatgtcat tgcgctgcca ttctccaaat  12780

tgcagttcgc gcttagctgg ataacgccac ggaatgatgt cgtcgtgcac aacaatggtg  12840

acttctacag cgcggagaat ctcgctctct ccaggggaag ccgaagtttc caaaaggtcg  12900

ttgatcaaag ctcgccgcgt tgtttcatca agccttacgg tcaccgtaac cagcaaatca  12960

atatcactgt gtggcttcag gccgccatcc actgcggagc cgtacaaatg tacggccagc  13020

aacgtcggtt cgagatggcg ctcgatgacg ccaactacct ctgatagttg agtcgatact  13080

tcggcgatca ccgcttccct catactcttc ctttttcaat attattgaag catttatcag  13140

ggttattgtc tcatgagcgg atacatattt gaatgtattt agaaaaataa acaaatagct  13200

agctcactcg gtcgctacgc tccgggcgtg agactgc                           13237
```

<210> SEQ ID NO 2
<211> LENGTH: 13237
<212> TYPE: DNA
<213> ORGANISM: Methylococcus capsulatus str. Bath
<220> FEATURE:
<221> NAME/KEY: misc_feature
<222> LOCATION: (1)..(13237)
<223> OTHER INFORMATION: pNH265

<400> SEQUENCE: 2

```
ttgtttcatc aagccttacg gtcaccgtaa ccagcaaatc aatatcactg tgtggcttca     60

ggccgccatc cactgcggag ccgtacaaat gtacggccag caacgtcggt tcgagatggc    120

gctcgatgac gccaactacc tctgatagtt gagtcgatac ttcggcgatc accgcttccc    180

tcatactctt cctttttcaa tattattgaa gcatttatca gggttattgt ctcatgagcg    240

gatacatatt tgaatgtatt tagaaaaata aacaaatagc tagctcactc ggtcgctacg    300

ctccgggcgt gagactgcgg cgggcgctgc ggacacatac aaagttaccc acagattccg    360

tggataagca ggggactaac atgtgaggca aaacagcagg gccgcgccgg tggcgttttt    420

ccataggctc cgccctcctg ccagagttca cataaacaga cgcttttccg gtgcatctgt    480

gggagccgtg aggctcaacc atgaatctga cagtacgggc gaaacccgac aggacttaaa    540

gatccccacc gtttccggct ggtcgctccc tcttgcgctc tcctgttccg accctgccgt    600

ttaccggata cctgttccgc ctttctccct tacgggaagt gtggcgcttt ctcatagctc    660

acacactggt atctcggctc ggtgtaggtc gttcgctcca agctgggctg taagcaagaa    720

ctccccgttc agcccgactg ctgcgcctta tccggtaact gttcacttga gtccaacccg    780

gaaaagcacg gtaaaacgcc actggcagca gccattggta actgggagtt cgcagaggat    840

ttgtttagct aaacacgcgg ttgctcttga agtgtgcgcc aaagtccggc tacactggaa    900

ggacagattt ggttgctgtg ctctgcgaaa gccagttacc acggttaagc agttccccaa    960

ctgacttaac cttcgatcaa accacctccc aatgtggttt tttcgtttac agggcaaaag   1020

attacgcgca gaaaaaaagg atctcaagaa gatcctttga tcttttctac tgaaccgctc   1080

tagatttcag tgcaatttat ctcttcaaat gtagcacctg aagtcagccc catacgatat   1140

aagttgtaat tctcatgtta gtcatgcccc gcgcccaccg gaaggagctg actgggttga   1200

aggctctcaa gggcatcggt cgagatcccg gtgcctaatg agtgagctaa cttttgacgg   1260
```

```
ctagctcagt cctagggata atgctagcac cagcctcgag ggaaaccacg taagctccgg   1320
cgtttaaaca cccataacag atacggactt tctcaaagga gagttatcag tgaaaatccg   1380
cccgttacat gaccgtgtca tcatcaaacg cttggaagaa gagcgtacct cggcgggcgg   1440
gattgtcatt ccagatagcg cagctgaaaa accgatgcgt ggtgaaatcc tggcagtggg   1500
caatggaaaa gtgcttgata atggagaggt acgtgcttta caggtgaaag tgggtgataa   1560
agtgctcttt gggaaatacg cgggtacgga ggttaaagta gatggggaag atgttgttgt   1620
catgcgtgaa gatgacattc tggctgtgtt agaatcttaa tccgcgcacg acactgaaca   1680
tacgaattta aggaataaag ataatggcga aagaagttgt gtatcgtggt agtgcgcgcc   1740
agcgtatgat gcagggtatt gaaattctcg ctcgcgccgc tattccaacg ctgggggcaa   1800
ccggcccgag cgtcatgatt caacatcgcg ccgatggtct gccacccatt tctacacgcg   1860
atggcgttac cgtagcgaat tctattgttt taaaagaccg tgtcgcgaac ctgggtgccc   1920
gcctgctgcg cgacgtagcc ggtacaatga gccgtgaagc cggcgacggc acgacgactg   1980
cgatcgtatt ggcccgccac atcgcccgtg agatgtttaa atcgctggcc gtgggtgcag   2040
atccgatcgc gctgaaacgt ggtatcgatc gcgccgttgc tcgtgtgtcc gaagatattg   2100
gggcgcgtgc gtggcgtggc gataaagaaa gcgtgatcct gggtgtcgct gctgtggcga   2160
cgaaaggcga accgggcgtt ggccgtctgc tgctggaggc tctcgatgca gtgggtgttc   2220
acggtgccgt ttctatcgaa ctgggccaac gtcgtgaaga tctgctggac gtcgtcgatg   2280
gctatcgctg ggaaaaaggt tatttatctc cctactttgt cacggaccgt gcccgcgaac   2340
tcgcggaact ggaggatgtc tacctgctca tgaccgaccg cgaagtggtt gacttcatcg   2400
accttgtacc tctgctggag gccgtgacgg aagcaggagg ctccctgctg attgccgcgg   2460
atcgtgtgca cgaaaaggcc ttagcggggc tgcttctgaa tcacgtgcgc ggtgtcttca   2520
aggccgtggc cgtaaccgct ccgggttttg gcgacaaacg cccgaaccgt ttacttgacc   2580
tggccgcgtt aaccggcggt cgtgccgtgc tcgaagctca aggcgaccgt ctggaccgtg   2640
ttaccctcgc ggatctgggc cgtgtgcgcc gtgccgtggt gtcggcagat gataccgcgc   2700
tgcttggcat cccgggcacc gaagctagcc gtgcacgcct cgaaggtctg cgtttagaag   2760
cagagcagta ccgtgcgctg aaaccagggc agggttctgc caccgggcgc ctgcacgaac   2820
ttgaagaaat tgaagcgcgc attgtgggtc tgtccggaaa gagcgccgtt tatcgcgtcg   2880
gaggtgtgac cgatgtggaa atgaaagagc gcatggttcg catcgaaaac gcttaccgtt   2940
cggtggtaag tgcgctggag gaaggcgtgc tccctggcgg tggtgtcggc tttctgggta   3000
gtatgccggt gcttgcggaa ttggaggccc gcgacgcaga tgaagctcgc gggattggga   3060
ttgtacgcag cgccttaacg gagcctcttc gtattatcgg cgaaaatagt ggcttgagcg   3120
gtgaagccgt tgttgccaaa gtcatggatc atgccaaccc gggatggggt tacgaccagg   3180
agtctggctc tttttgcgac ctgcatgcgc gtgggatctg ggatgctgct aaagtgttac   3240
gtctcgcgtt ggagaaggca gcctctgttg ctgggacctt tctgacaacc gaagctgttg   3300
ttctcgaaat tccggataca gatgcgttcg cagggttcag tgcagaatgg gctgccgcca   3360
cgcgcgaaga tccgcgcgta tgagtttaaa cgcggccgca atttgaacgc acccataaca   3420
gatacggact ttctcaaagg agagttatca atgaatattc gtccattgca tgatcgcgtg   3480
atcgtcaagc gtaaagaagt tgaaactaaa tctgctggcg gcatcgttct gaccggctct   3540
gcagcggcta aatccacccg cggcgaagtg ctggctgtcg gcaatggccg tatccttgaa   3600
```

-continued

```
aatggcgaag tgaagccgct ggatgtgaaa gttggcgaca tcgttatttt caacgatggc   3660
tacggtgtga aatctgagaa gatcgacaat gaagaagtgt tgatcatgtc cgaaagcgac   3720
attctggcaa ttgttgaagc gtaatccgcg cacgacactg aacatacgaa tttaaggaat   3780
aaagataatg gcagctaaag acgtaaaatt cggtaacgac gctcgtgtga aaatgctgcg   3840
cggcgtaaac gtactggcag atgcagtgaa agttaccctc ggtccaaaag gccgtaacgt   3900
agttctggat aaatctttcg gtgcaccgac catcaccaaa gatggtgttt ccgttgctcg   3960
tgaaatcgaa ctggaagaca agttcgaaaa tatgggtgcg cagatggtga aagaagttgc   4020
ctctaaagca aacgacgctg caggcgacgg taccaccact gcaaccgtac tggctcaggc   4080
tatcatcact gaaggtctga aagctgttgc tgcgggcatg aacccgatgg acctgaaacg   4140
tggtatcgac aaagcggtta ccgctgcagt tgaagaactg aaagcgctgt ccgtaccatg   4200
ctctgactct aaagcgattg ctcaggttgg taccatctcc gctaactccg acgaaaccgt   4260
aggtaaactg atcgctgaag cgatggacaa agtcggtaaa gaaggcgtta tcaccgttga   4320
agacggtacc ggtctgcagg acgaactgga cgtggttgaa ggtatgcagt tcgaccgtgg   4380
ctacctgtct ccttacttca tcaacaagcc ggaaactggc gcagtagaac tggaaagccc   4440
gttcatcctg ctggctgaca agaaaatctc caacatccgc gaaatgctgc cggttctgga   4500
agctgttgcc aaagcaggca aaccgctgct gatcatcgct gaagatgtag aaggcgaagc   4560
gctggcaact ctggttgtta acaccatgcg tggcatcgtg aaagtcgctg cggttaaagc   4620
accgggcttc ggcgatcgtc gtaaagctat gctgcaggat atcgcaaccc tgactggcgg   4680
taccgtgatc tctgaagaga tcggtatgga gctggaaaaa gcaaccctgg aagacctggg   4740
tcaggctaaa cgtgttgtga tcaacaaaga caccaccact atcatcgatg gcgtgggtga   4800
agaagctgca atccagggcc gtgttgctca gatccgtcag cagattgaag aagcaacttc   4860
tgactacgac cgtgaaaaac tgcaggaacg cgtagcgaaa ctggcaggcg gcgttgcagt   4920
tatcaaagtg ggtgctgcta ccgaagttga aatgaaagag aaaaaagcac gcgttgaaga   4980
tgccctgcac gcgacccgtg ctgcggtaga agaaggcgtg gttgctggtg gtggtgttgc   5040
gctgatccgc gtagcgtcta aactggctga cctgcgtggt cagaacgaag accagaacgt   5100
gggtatcaaa gttgcactgc gtgcaatgga agctccgctg cgtcagatcg tattgaactg   5160
cggcgaagaa ccgtctgttg ttgctaacac cgttaaaggc ggcgacggca actacggtta   5220
caacgcagca accgaagaat acggcaacat gatcgacatg ggtatcctgg atccaaccaa   5280
agtaactcgt tctgctctgc agtacgcagc ttctgtggct ggcctgatga tcaccaccga   5340
atgcatggtt accgacctgc cgaaaaacga tgcagctgac ttaggcgctg ctggcggtat   5400
gggcggcatg atgtaagttt aaacgcggcc gcaatttgaa cgccagcaca tggactctcg   5460
agtctactag cgcagcttaa ttaacctagg ctgctgccac cgctgagcaa taactagcat   5520
aaccccttgg ggcctctaaa cgggtcttga ggggtttttt gctgaaacct caggcatttg   5580
agaagcacac ggtcacactg cttccggtag tcaataaacc ggtaaaccag caatagacat   5640
aagcggtgca taatgtgcct gtcaaatgga cgaagcaggg attctgcaaa ccctatgcta   5700
ctccgtcaag ccgtcaattg tctgattcgt taccaattat gacaacttga cggctacatc   5760
attcactttt tcttcacaac cggcacggaa ctcgctcggg ctggccccgg tgcatttttt   5820
aaatacccgc gagaaataga gttgatcgtc aaaaccaaca ttgcgaccga cggtggcgat   5880
aggcatccgg gtggtgctca aaagcagctt cgcctggctg atacgttggt cctcgcgcca   5940
gcttaagacg ctaatcccta actgctggcg gaaaagatgt gacagacgcg acggcgacaa   6000
```

```
gcaaacatgc tgtgcgacgc tggcgatatc aaaattgctg tctgccaggt gatcgctgat   6060
gtactgacaa gcctcgcgta cccgattatc catcggtgga tggagcgact cgttaatcgc   6120
ttccatgcgc cgcagtaaca attgctcaag cagatttatc gccagcagct ccgaatagcg   6180
cccttcccct tgcccggcgt taatgatttg cccaaacagg tcgctgaaat gcggctggtg   6240
cgcttcatcc gggcgaaaga accccgtatt ggcaaatatt gacggccagt taagccattc   6300
atgccagtag gcgcgcggac gaaagtaaac ccactggtga taccattcgc gagcctccgg   6360
atgacgaccg tagtgatgaa tctctcctgg cgggaacagc aaaatatcac ccggtcggca   6420
aacaaattct cgtccctgat ttttcaccac cccctgaccg cgaatggtga gattgagaat   6480
ataacctttc attcccagcg gtcggtcgat aaaaaaatcg agataaccgt tggcctcaat   6540
cggcgttaaa cccgccacca gatgggcatt aaacgagtat cccggcagca ggggatcatt   6600
ttgcgcttca gccatacttt tcatactccc gccattcaga gaagaaacca attgtccata   6660
ttgcatcaga cattgccgtc actgcgtctt ttactggctc ttctcgctaa ccaaaccggt   6720
aaccccgctt attaaaagca ttctgtaaca aagcgggacc aaagccatga caaaaacgcg   6780
taacaaaagt gtctataatc acggcagaaa agtccacatt gattatttgc acggcgtcac   6840
actttgctat gccatagcat ttttatccat aagattagcg gatcctacct gacgcttttt   6900
atcgcaactc tggacaatgt ctccataccc gtttttttgg gcgacctcgt cggaggttgt   6960
atgtccggtg ttccgtgacg tcatcgggca ttcatcattc atagaatgtg ttacggagga   7020
aacaagtaat ggcacttagc accgcaacca aggccgcgac ggacgcgctg gctgccaatc   7080
gggcacccac cagcgtgaat gcacaggaag tgcaccgttg gctccagagc ttcaactggg   7140
atttcaagaa caaccggacc aagtacgcca ccaagtacaa gatggcgaac gagaccaagg   7200
aacagttcaa gctgatcgcc aaggaaatatg cgcgcatgga ggcagtcaag gacgaaaggc   7260
agttcggtag cctgcaggat gcgctgaccc gcctcaacgc cggtgttcgc gttcatccga   7320
agtggaacga gaccatgaaa gtggtttcga acttcctgga agtgggcgaa tacaacgcca   7380
tcgccgctac cgggatgctg tgggattccg cccaggcggc ggaacagaag aacggctatc   7440
tggcccaggt gttggatgaa atccgccaca cccaccagtg tgcctacgtc aactactact   7500
tcgcgaagaa cggccaggac ccggccggtc acaacgatgc tcgccgcacc cgtaccatcg   7560
gtccgctgtg gaagggcatg aagcgcgtgt tttccgacgg cttcatttcc ggcgacgccg   7620
tggaatgctc cctcaacctg cagctggtgg gtgaggcctg cttcaccaat ccgctgatcg   7680
tcgcagtgac cgaatgggct gccgccaacg gcgatgaaat caccccgacg gtgttcctgt   7740
cgatcgagac cgacgaactg cgccacatgg ccaacggtta ccagaccgtc gtttccatcg   7800
ccaacgatcc ggcttccgcc aagtatctca acacggacct gaacaacgcc ttctggaccc   7860
agcagaagta cttcacgccg gtgttgggca tgctgttcga gtatggctcc aagttcaagg   7920
tcgagccgtg ggtcaagacg tggaaccgct gggtgtacga ggactggggc ggcatctgga   7980
tcggccgtct gggcaagtac ggggtggagt cgccgcgcag cctcaaggac gccaagcagg   8040
acgcttactg ggctcaccac gacctgtatc tgctggctta tgcgctgtgg ccgaccggct   8100
tcttccgtct ggcgctgccg gatcaggaag aaatggagtg gttcgaggcc aactaccccg   8160
gctggtacga ccactacggc aagatctacg aggaatggcg cgcccgcggt tgcgaggatc   8220
cgtcctcggg cttcatcccg ctgatgtggt tcatcgaaaa caaccatccc atctacatcg   8280
atcgcgtgtc gcaagtgccg ttctgcccga gcttggccaa gggcgccagc accctgcgcg   8340
```

```
tgcacgagta caacggccag atgcacacct tcagcgacca gtggggcgag cgcatgtggc   8400
tggccgagcc ggagcgctac gagtgccaga acatcttcga acagtacgaa ggacgcgaac   8460
tgtcggaagt gatcgccgaa ctgcacgggc tgcgcagtga tggcaagacc ctgatcgccc   8520
agccgcatgt ccgtggcgac aagctgtgga cgttggacga tatcaaacgc ctgaactgcg   8580
tcttcaagaa cccggtgaag gcattcaatt gaaacgggtg tcgggctccg tcacagggcg   8640
gggcccgacg cacgatcgtt cgatcaacct caaaccaaaa aggaacatcg atatgagcat   8700
gttaggagaa agacgccgcg gtctgaccga tccggaaatg gcggccgtca ttttgaaggc   8760
gcttcctgaa gctccgctgg acggcaacaa caagatgggt tatttcgtca ccccccgctg   8820
gaaacgcttg acggaatatg aagccctgac cgtttatgcg cagcccaacg ccgactggat   8880
cgccggcggc ctggactggg gcgactggac ccagaaattc cacggcggcc gcccttcctg   8940
gggcaacgag accacggagc tgcgcaccgt cgactggttc aagcaccgtg acccgctccg   9000
ccgttggcat gcgccgtacg tcaaggacaa ggccgaggaa tggcgctaca ccgaccgctt   9060
cctgcagggt tactccgccg acggtcagat ccgggcgatg aacccgacct ggcgggacga   9120
gttcatcaac cggtattggg gcgccttcct gttcaacgaa tacggattgt tcaacgctca   9180
ttcgcagggc gcccgggagg cgctgtcgga cgtaacccgc gtcagcctgg ctttctgggg   9240
cttcgacaag atcgacatcg cccagatgat ccaactcgaa cggggtttcc tcgccaagat   9300
cgtacccggt ttcgacgagt ccacagcggt gccgaaggcc gaatggacga acggggaggt   9360
ctacaagagc gcccgtctgg ccgtggaagg gctgtggcag gaggtgttcg actggaacga   9420
gagcgctttc tcggtgcacg ccgtctatga cgcgctgttc ggtcagttcg tccgccgcga   9480
gttctttcag cggctggctc cccgcttcgg cgacaatctg acgccattct tcatcaacca   9540
ggcccagaca tacttccaga tcgccaagca gggcgtacag gatctgtatt acaactgtct   9600
gggtgacgat ccggagttca gcgattacaa ccgtaccgtg atgcgcaact ggaccggcaa   9660
gtggctggag cccacgatcg ccgctctgcg cgacttcatg gggctgtttg cgaagctgcc   9720
ggcgggcacc actgacaagg aagaaatcac cgcgtccctg taccgggtgg tcgacgactg   9780
gatcgaggac tacgccagca ggatcgactt caaggcggac cgcgatcaga tcgttaaagc   9840
ggttctggca ggattgaaat aatagaggaa ctattacgat gagcgtaaac agcaacgcat   9900
acgacgccgg catcatgggc ctgaaaggca aggacttcgc cgatcagttc tttgccgacg   9960
aaaaccaagt ggtccatgaa agcgacacgg tcgttctggt cctcaagaag tcggacgaga  10020
tcaatacctt tatcgaggag atccttctga cggactacaa gaagaacgtc aatccgacgg  10080
taaacgtgga agaccgcgcg ggttactggt ggatcaaggc caacggcaag atcgaggtcg  10140
attgcgacga gatttccgag ctgttggggc ggcagttcaa cgtctacgac ttcctcgtcg  10200
acgtttcctc caccatcggc cggcctata ccctgggcaa caagttcacc attaccagtg  10260
agctgatggg cctggaccgc aagctcgaag actatcacgc ttaaggagaa tgacatggcg  10320
aaactgggta tacacagcaa cgacacccgc gacgcctggg tgaacaagat cgcgcagctc  10380
aacaccctgg aaaaagcggc cgagatgctg aagcagttcc ggatggacca caccacgccg  10440
ttccgcaaca gctacgaact ggacaacgac tacctctgga tcgaggccaa gctcgaagag  10500
aaggtcgccg tcctcaaggc acgcgccttc aacgaggtgg acttccgtca taagaccgct  10560
ttcggcgagg atgccaagtc cgttctggac ggcaccgtcg cgaagatgaa cgcggccaag  10620
gacaagtggg aggcggagaa gatccatatc ggtttccgcc aggcctacaa gccgccgatc  10680
atgccggtga actatttcct ggacggcgag cgtcagttgg ggacccggct gatggaactg  10740
```

```
cgcaacctca actactacga cacgccgctg gaagaactgc gcaaacagcg cggtgtgcgg  10800
gtggtgcatc tgcagtcgcc gcactgaagg gaggaagtct cgccctggac gcgacggcat  10860
cgccgtgaag tccagggggc agggatgccg ttccgggccg gcaggctggc ccggaatctc  10920
tggttttcag gggcgtgcc ggtccacggc tccccccctcc atctttcgta aggaaatcac  10980
catggtcgaa tcggcatttc agccattttc gggcgacgca gacgaatggt tcgaggaacc  11040
acggccccag gccggtttct tcccttccgc ggactggcat ctgctcaaac gggacgagac  11100
ctacgcagcc tatgccaagg atctcgattt catgtggcgg tgggtcatcg tccgggaaga  11160
aaggatcgtc caggagggtt gctcgatcag cctggagtcg tcgatccgcg ccgtgacgca  11220
cgtactgaat tattttggta tgaccgaaca acgcgccccg gcagaggacc ggaccggcgg  11280
agttcaacat tgaacaggta agtttatgca gcgagttcac actatcacgg cggtgacgga  11340
ggatggcgaa tcgctccgct tcgaatgccg ttcggacgag gacgtcatca ccgccgccct  11400
gcgccagaac atctttctga tgtcgtcctg ccgggagggc ggctgtgcga cctgcaaggc  11460
cttgtgcagc gaaggggact acgacctcaa gggctgcagc gttcaggcgc tgccgccgga  11520
agaggaggag gaagggttgg tgttgttgtg ccggacctac ccgaagaccg acctggaaat  11580
cgaactgccc tatacccatt gccgcatcag ttttggtgag gtcggcagtt tcgaggcgga  11640
ggtcgtcggc ctcaactggg tttcgagcaa caccgtccag tttcttttgc agaagcggcc  11700
cgacgagtgc ggcaaccgtg gcgtgaaatt cgaacccggt cagttcatgg acctgaccat  11760
ccccggcacc gatgtctccc gctcctactc gccggcgaac cttcctaatc ccgaaggccg  11820
cctggagttc ctgatccgcg tgttaccgga gggacggttt tcggactacc tgcgcaatga  11880
cgcgcgtgtc ggacaggtcc tctcggtcaa agggccactg ggcgtgttcg gtctcaagga  11940
gcggggcatg gcgccgcgct atttcgtggc cggcggcacc gggttggcgc cggtggtctc  12000
gatggtgcgg cagatgcagg agtggaccgc gccgaacgag acccgcatct atttcggtgt  12060
gaacaccgag ccggaattgt tctacatcga cgagctcaaa tccctggaac gatcgatgcg  12120
caatctcacc gtgaaggcct gtgtctggca cccgagcggg gactgggaag gcgagcaggg  12180
ctcgcccatc gatgcgttgc gggaagacct ggagtcctcc gacgccaacc cggacattta  12240
tttgtgcggt ccgccgggca tgatcgatgc cgcctgcgag ctggtacgca gccgcggtat  12300
ccccggcgaa caggtcttct tcgaaaaatt cctgccgtcc ggggcggcct gaaccgggga  12360
agtaccgtga ccaccgagca gttcccgccc caattcctgc gtgaaatgat cgagcagctg  12420
gacgccagca tccaggagct cgcacgcaag gaaaagggac ttgcggcatc cctgggcacg  12480
ggccgggtcg ccgagctcaa ggaatactgg gaccacgttg ttacaaccaa ttaaccaatt  12540
ctgactattt aacgaccctg ccctgaaccg acgaccgggt catcgtggcc ggatcttgcg  12600
gcccctcggc ttgaacgaat tgttagacat tatttgccga ctaccttggt gatctcgcct  12660
ttcacgtagt ggacaaattc ttccaactga tctgcgcgcg aggccaagcg atcttcttct  12720
tgtccaagat aagcctgtct agcttcaagt atgacgggct gatactgggc cggcaggcgc  12780
tccattgccc agtcggcagc gacatccttc ggcgcgattt tgccggttac tgcgctgtac  12840
caaatgcggg acaacgtaag cactacattt cgctcatcgc cagcccagtc gggcggcgag  12900
ttccatagcg ttaaggtttc atttagcgcc tcaaatagat cctgttcagg aaccggatca  12960
aagagttcct ccgccgctgg acctaccaag gcaacgctat gttctcttgc ttttgtcagc  13020
aagatagcca gatcaatgtc gatcgtggct ggctcgaaga tacctgcaag aatgtcattg  13080
```

```
cgctgccatt ctccaaattg cagttcgcgc ttagctggat aacgccacgg aatgatgtcg  13140

tcgtgcacaa caatggtgac ttctacagcg cggagaatct cgctctctcc aggggaagcc  13200

gaagtttcca aaaggtcgtt gatcaaagct cgccgcg                           13237


<210> SEQ ID NO 3
<211> LENGTH: 527
<212> TYPE: PRT
<213> ORGANISM: Methylococcus capsulatus str. Bath
<220> FEATURE:
<221> NAME/KEY: misc_feature
<222> LOCATION: (1)..(527)
<223> OTHER INFORMATION: mmoX

<400> SEQUENCE: 3

Met Ala Leu Ser Thr Ala Thr Lys Ala Ala Thr Asp Ala Leu Ala Ala
1               5                   10                  15

Asn Arg Ala Pro Thr Ser Val Asn Ala Gln Glu Val His Arg Trp Leu
            20                  25                  30

Gln Ser Phe Asn Trp Asp Phe Lys Asn Asn Arg Thr Lys Tyr Ala Thr
        35                  40                  45

Lys Tyr Lys Met Ala Asn Glu Thr Lys Glu Gln Phe Lys Leu Ile Ala
    50                  55                  60

Lys Glu Tyr Ala Arg Met Glu Ala Val Lys Asp Glu Arg Gln Phe Gly
65                  70                  75                  80

Ser Leu Gln Asp Ala Leu Thr Arg Leu Asn Ala Gly Val Arg Val His
                85                  90                  95

Pro Lys Trp Asn Glu Thr Met Lys Val Val Ser Asn Phe Leu Glu Val
            100                 105                 110

Gly Glu Tyr Asn Ala Ile Ala Ala Thr Gly Met Leu Trp Asp Ser Ala
        115                 120                 125

Gln Ala Ala Glu Gln Lys Asn Gly Tyr Leu Ala Gln Val Leu Asp Glu
    130                 135                 140

Ile Arg His Thr His Gln Cys Ala Tyr Val Asn Tyr Tyr Phe Ala Lys
145                 150                 155                 160

Asn Gly Gln Asp Pro Ala Gly His Asn Asp Ala Arg Arg Thr Arg Thr
                165                 170                 175

Ile Gly Pro Leu Trp Lys Gly Met Lys Arg Val Phe Ser Asp Gly Phe
            180                 185                 190

Ile Ser Gly Asp Ala Val Glu Cys Ser Leu Asn Leu Gln Leu Val Gly
        195                 200                 205

Glu Ala Cys Phe Thr Asn Pro Leu Ile Val Ala Val Thr Glu Trp Ala
    210                 215                 220

Ala Ala Asn Gly Asp Glu Ile Thr Pro Thr Val Phe Leu Ser Ile Glu
225                 230                 235                 240

Thr Asp Glu Leu Arg His Met Ala Asn Gly Tyr Gln Thr Val Val Ser
                245                 250                 255

Ile Ala Asn Asp Pro Ala Ser Ala Lys Tyr Leu Asn Thr Asp Leu Asn
            260                 265                 270

Asn Ala Phe Trp Thr Gln Gln Lys Tyr Phe Thr Pro Val Leu Gly Met
        275                 280                 285

Leu Phe Glu Tyr Gly Ser Lys Phe Lys Val Glu Pro Trp Val Lys Thr
    290                 295                 300

Trp Asn Arg Trp Val Tyr Glu Asp Trp Gly Gly Ile Trp Ile Gly Arg
305                 310                 315                 320

Leu Gly Lys Tyr Gly Val Glu Ser Pro Arg Ser Leu Lys Asp Ala Lys
```

```
                325                 330                 335

Gln Asp Ala Tyr Trp Ala His His Asp Leu Tyr Leu Leu Ala Tyr Ala
            340                 345                 350

Leu Trp Pro Thr Gly Phe Phe Arg Leu Ala Leu Pro Asp Gln Glu Glu
        355                 360                 365

Met Glu Trp Phe Glu Ala Asn Tyr Pro Gly Trp Tyr Asp His Tyr Gly
    370                 375                 380

Lys Ile Tyr Glu Glu Trp Arg Ala Arg Gly Cys Glu Asp Pro Ser Ser
385                 390                 395                 400

Gly Phe Ile Pro Leu Met Trp Phe Ile Glu Asn Asn His Pro Ile Tyr
                405                 410                 415

Ile Asp Arg Val Ser Gln Val Pro Phe Cys Pro Ser Leu Ala Lys Gly
            420                 425                 430

Ala Ser Thr Leu Arg Val His Glu Tyr Asn Gly Gln Met His Thr Phe
        435                 440                 445

Ser Asp Gln Trp Gly Glu Arg Met Trp Leu Ala Glu Pro Glu Arg Tyr
    450                 455                 460

Glu Cys Gln Asn Ile Phe Glu Gln Tyr Glu Gly Arg Glu Leu Ser Glu
465                 470                 475                 480

Val Ile Ala Glu Leu His Gly Leu Arg Ser Asp Gly Lys Thr Leu Ile
                485                 490                 495

Ala Gln Pro His Val Arg Gly Asp Lys Leu Trp Thr Leu Asp Asp Ile
            500                 505                 510

Lys Arg Leu Asn Cys Val Phe Lys Asn Pro Val Lys Ala Phe Asn
        515                 520                 525


<210> SEQ ID NO 4
<211> LENGTH: 389
<212> TYPE: PRT
<213> ORGANISM: Methylococcus capsulatus str. Bath
<220> FEATURE:
<221> NAME/KEY: misc_feature
<222> LOCATION: (1)..(389)
<223> OTHER INFORMATION: mmoY

<400> SEQUENCE: 4

Met Ser Met Leu Gly Glu Arg Arg Arg Gly Leu Thr Asp Pro Glu Met
1               5                   10                  15

Ala Ala Val Ile Leu Lys Ala Leu Pro Glu Ala Pro Leu Asp Gly Asn
            20                  25                  30

Asn Lys Met Gly Tyr Phe Val Thr Pro Arg Trp Lys Arg Leu Thr Glu
        35                  40                  45

Tyr Glu Ala Leu Thr Val Tyr Ala Gln Pro Asn Ala Asp Trp Ile Ala
    50                  55                  60

Gly Gly Leu Asp Trp Gly Asp Trp Thr Gln Lys Phe His Gly Gly Arg
65                  70                  75                  80

Pro Ser Trp Gly Asn Glu Thr Thr Glu Leu Arg Thr Val Asp Trp Phe
                85                  90                  95

Lys His Arg Asp Pro Leu Arg Arg Trp His Ala Pro Tyr Val Lys Asp
            100                 105                 110

Lys Ala Glu Glu Trp Arg Tyr Thr Asp Arg Phe Leu Gln Gly Tyr Ser
        115                 120                 125

Ala Asp Gly Gln Ile Arg Ala Met Asn Pro Thr Trp Arg Asp Glu Phe
    130                 135                 140

Ile Asn Arg Tyr Trp Gly Ala Phe Leu Phe Asn Glu Tyr Gly Leu Phe
145                 150                 155                 160
```

Asn Ala His Ser Gln Gly Ala Arg Glu Ala Leu Ser Asp Val Thr Arg
165 170 175

Val Ser Leu Ala Phe Trp Gly Phe Asp Lys Ile Asp Ile Ala Gln Met
180 185 190

Ile Gln Leu Glu Arg Gly Phe Leu Ala Lys Ile Val Pro Gly Phe Asp
195 200 205

Glu Ser Thr Ala Val Pro Lys Ala Glu Trp Thr Asn Gly Glu Val Tyr
210 215 220

Lys Ser Ala Arg Leu Ala Val Glu Gly Leu Trp Gln Glu Val Phe Asp
225 230 235 240

Trp Asn Glu Ser Ala Phe Ser Val His Ala Val Tyr Asp Ala Leu Phe
245 250 255

Gly Gln Phe Val Arg Arg Glu Phe Phe Gln Arg Leu Ala Pro Arg Phe
260 265 270

Gly Asp Asn Leu Thr Pro Phe Phe Ile Asn Gln Ala Gln Thr Tyr Phe
275 280 285

Gln Ile Ala Lys Gln Gly Val Gln Asp Leu Tyr Tyr Asn Cys Leu Gly
290 295 300

Asp Asp Pro Glu Phe Ser Asp Tyr Asn Arg Thr Val Met Arg Asn Trp
305 310 315 320

Thr Gly Lys Trp Leu Glu Pro Thr Ile Ala Ala Leu Arg Asp Phe Met
325 330 335

Gly Leu Phe Ala Lys Leu Pro Ala Gly Thr Thr Asp Lys Glu Glu Ile
340 345 350

Thr Ala Ser Leu Tyr Arg Val Val Asp Asp Trp Ile Glu Asp Tyr Ala
355 360 365

Ser Arg Ile Asp Phe Lys Ala Asp Arg Asp Gln Ile Val Lys Ala Val
370 375 380

Leu Ala Gly Leu Lys
385

<210> SEQ ID NO 5
<211> LENGTH: 170
<212> TYPE: PRT
<213> ORGANISM: Methylococcus capsulatus str. Bath
<220> FEATURE:
<221> NAME/KEY: misc_feature
<222> LOCATION: (1)..(170)
<223> OTHER INFORMATION: mmoZ

<400> SEQUENCE: 5

Met Ala Lys Leu Gly Ile His Ser Asn Asp Thr Arg Asp Ala Trp Val
1 5 10 15

Asn Lys Ile Ala Gln Leu Asn Thr Leu Glu Lys Ala Ala Glu Met Leu
20 25 30

Lys Gln Phe Arg Met Asp His Thr Thr Pro Phe Arg Asn Ser Tyr Glu
35 40 45

Leu Asp Asn Asp Tyr Leu Trp Ile Glu Ala Lys Leu Glu Glu Lys Val
50 55 60

Ala Val Leu Lys Ala Arg Ala Phe Asn Glu Val Asp Phe Arg His Lys
65 70 75 80

Thr Ala Phe Gly Glu Asp Ala Lys Ser Val Leu Asp Gly Thr Val Ala
85 90 95

Lys Met Asn Ala Ala Lys Asp Lys Trp Glu Ala Glu Lys Ile His Ile
100 105 110

```
Gly Phe Arg Gln Ala Tyr Lys Pro Pro Ile Met Pro Val Asn Tyr Phe
        115                 120                 125

Leu Asp Gly Glu Arg Gln Leu Gly Thr Arg Leu Met Glu Leu Arg Asn
    130                 135                 140

Leu Asn Tyr Tyr Asp Thr Pro Leu Glu Glu Leu Arg Lys Gln Arg Gly
145                 150                 155                 160

Val Arg Val Val His Leu Gln Ser Pro His
                165                 170


<210> SEQ ID NO 6
<211> LENGTH: 141
<212> TYPE: PRT
<213> ORGANISM: Methylococcus capsulatus str. Bath
<220> FEATURE:
<221> NAME/KEY: misc_feature
<222> LOCATION: (1)..(141)
<223> OTHER INFORMATION: mmoB

<400> SEQUENCE: 6

Met Ser Val Asn Ser Asn Ala Tyr Asp Ala Gly Ile Met Gly Leu Lys
1               5                   10                  15

Gly Lys Asp Phe Ala Asp Gln Phe Phe Ala Asp Glu Asn Gln Val Val
            20                  25                  30

His Glu Ser Asp Thr Val Val Leu Val Leu Lys Lys Ser Asp Glu Ile
        35                  40                  45

Asn Thr Phe Ile Glu Glu Ile Leu Leu Thr Asp Tyr Lys Lys Asn Val
    50                  55                  60

Asn Pro Thr Val Asn Val Glu Asp Arg Ala Gly Tyr Trp Trp Ile Lys
65                  70                  75                  80

Ala Asn Gly Lys Ile Glu Val Asp Cys Asp Glu Ile Ser Glu Leu Leu
                85                  90                  95

Gly Arg Gln Phe Asn Val Tyr Asp Phe Leu Val Asp Val Ser Ser Thr
            100                 105                 110

Ile Gly Arg Ala Tyr Thr Leu Gly Asn Lys Phe Thr Ile Thr Ser Glu
        115                 120                 125

Leu Met Gly Leu Asp Arg Lys Leu Glu Asp Tyr His Ala
    130                 135                 140


<210> SEQ ID NO 7
<211> LENGTH: 348
<212> TYPE: PRT
<213> ORGANISM: Methylococcus capsulatus str. Bath
<220> FEATURE:
<221> NAME/KEY: misc_feature
<222> LOCATION: (1)..(348)
<223> OTHER INFORMATION: mmoC

<400> SEQUENCE: 7

Met Gln Arg Val His Thr Ile Thr Ala Val Thr Glu Asp Gly Glu Ser
1               5                   10                  15

Leu Arg Phe Glu Cys Arg Ser Asp Glu Asp Val Ile Thr Ala Ala Leu
            20                  25                  30

Arg Gln Asn Ile Phe Leu Met Ser Ser Cys Arg Glu Gly Gly Cys Ala
        35                  40                  45

Thr Cys Lys Ala Leu Cys Ser Glu Gly Asp Tyr Asp Leu Lys Gly Cys
    50                  55                  60

Ser Val Gln Ala Leu Pro Pro Glu Glu Glu Glu Glu Gly Leu Val Leu
65                  70                  75                  80

Leu Cys Arg Thr Tyr Pro Lys Thr Asp Leu Glu Ile Glu Leu Pro Tyr
```

```
                85                  90                  95

Thr His Cys Arg Ile Ser Phe Gly Glu Val Gly Ser Phe Glu Ala Glu
            100                 105                 110

Val Val Gly Leu Asn Trp Val Ser Ser Asn Thr Val Gln Phe Leu Leu
        115                 120                 125

Gln Lys Arg Pro Asp Glu Cys Gly Asn Arg Gly Val Lys Phe Glu Pro
    130                 135                 140

Gly Gln Phe Met Asp Leu Thr Ile Pro Gly Thr Asp Val Ser Arg Ser
145                 150                 155                 160

Tyr Ser Pro Ala Asn Leu Pro Asn Pro Glu Gly Arg Leu Glu Phe Leu
                165                 170                 175

Ile Arg Val Leu Pro Glu Gly Arg Phe Ser Asp Tyr Leu Arg Asn Asp
            180                 185                 190

Ala Arg Val Gly Gln Val Leu Ser Val Lys Gly Pro Leu Gly Val Phe
        195                 200                 205

Gly Leu Lys Glu Arg Gly Met Ala Pro Arg Tyr Phe Val Ala Gly Gly
    210                 215                 220

Thr Gly Leu Ala Pro Val Val Ser Met Val Arg Gln Met Gln Glu Trp
225                 230                 235                 240

Thr Ala Pro Asn Glu Thr Arg Ile Tyr Phe Gly Val Asn Thr Glu Pro
                245                 250                 255

Glu Leu Phe Tyr Ile Asp Glu Leu Lys Ser Leu Glu Arg Ser Met Arg
            260                 265                 270

Asn Leu Thr Val Lys Ala Cys Val Trp His Pro Ser Gly Asp Trp Glu
        275                 280                 285

Gly Glu Gln Gly Ser Pro Ile Asp Ala Leu Arg Glu Asp Leu Glu Ser
    290                 295                 300

Ser Asp Ala Asn Pro Asp Ile Tyr Leu Cys Gly Pro Pro Gly Met Ile
305                 310                 315                 320

Asp Ala Ala Cys Glu Leu Val Arg Ser Arg Gly Ile Pro Gly Glu Gln
                325                 330                 335

Val Phe Phe Glu Lys Phe Leu Pro Ser Gly Ala Ala
            340                 345


<210> SEQ ID NO 8
<211> LENGTH: 103
<212> TYPE: PRT
<213> ORGANISM: Methylococcus capsulatus str. Bath
<220> FEATURE:
<221> NAME/KEY: misc_feature
<222> LOCATION: (1)..(103)
<223> OTHER INFORMATION: mmoD

<400> SEQUENCE: 8

Met Val Glu Ser Ala Phe Gln Pro Phe Ser Gly Asp Ala Asp Glu Trp
1               5                   10                  15

Phe Glu Glu Pro Arg Pro Gln Ala Gly Phe Phe Pro Ser Ala Asp Trp
            20                  25                  30

His Leu Leu Lys Arg Asp Glu Thr Tyr Ala Ala Tyr Ala Lys Asp Leu
        35                  40                  45

Asp Phe Met Trp Arg Trp Val Ile Val Arg Glu Glu Arg Ile Val Gln
    50                  55                  60

Glu Gly Cys Ser Ile Ser Leu Glu Ser Ser Ile Arg Ala Val Thr His
65                  70                  75                  80

Val Leu Asn Tyr Phe Gly Met Thr Glu Gln Arg Ala Pro Ala Glu Asp
                85                  90                  95
```

```
Arg Thr Gly Gly Val Gln His
            100


<210> SEQ ID NO 9
<211> LENGTH: 559
<212> TYPE: PRT
<213> ORGANISM: Methylococcus capsulatus str. Bath
<220> FEATURE:
<221> NAME/KEY: misc_feature
<222> LOCATION: (1)..(559)
<223> OTHER INFORMATION: groEL-2

<400> SEQUENCE: 9

Met Ala Lys Glu Val Val Tyr Arg Gly Ser Ala Arg Gln Arg Met Met
1               5                   10                  15

Gln Gly Ile Glu Ile Leu Ala Arg Ala Ala Ile Pro Thr Leu Gly Ala
            20                  25                  30

Thr Gly Pro Ser Val Met Ile Gln His Arg Ala Asp Gly Leu Pro Pro
        35                  40                  45

Ile Ser Thr Arg Asp Gly Val Thr Val Ala Asn Ser Ile Val Leu Lys
    50                  55                  60

Asp Arg Val Ala Asn Leu Gly Ala Arg Leu Leu Arg Asp Val Ala Gly
65                  70                  75                  80

Thr Met Ser Arg Glu Ala Gly Asp Gly Thr Thr Thr Ala Ile Val Leu
                85                  90                  95

Ala Arg His Ile Ala Arg Glu Met Phe Lys Ser Leu Ala Val Gly Ala
            100                 105                 110

Asp Pro Ile Ala Leu Lys Arg Gly Ile Asp Arg Ala Val Ala Arg Val
        115                 120                 125

Ser Glu Asp Ile Gly Ala Arg Ala Trp Arg Gly Asp Lys Glu Ser Val
    130                 135                 140

Ile Leu Gly Val Ala Ala Val Ala Thr Lys Gly Glu Pro Gly Val Gly
145                 150                 155                 160

Arg Leu Leu Leu Glu Ala Leu Asp Ala Val Gly Val His Gly Ala Val
                165                 170                 175

Ser Ile Glu Leu Gly Gln Arg Arg Glu Asp Leu Leu Asp Val Val Asp
            180                 185                 190

Gly Tyr Arg Trp Glu Lys Gly Tyr Leu Ser Pro Tyr Phe Val Thr Asp
        195                 200                 205

Arg Ala Arg Glu Leu Ala Glu Leu Glu Asp Val Tyr Leu Leu Met Thr
    210                 215                 220

Asp Arg Glu Val Val Asp Phe Ile Asp Leu Val Pro Leu Leu Glu Ala
225                 230                 235                 240

Val Thr Glu Ala Gly Gly Ser Leu Leu Ile Ala Ala Asp Arg Val His
                245                 250                 255

Glu Lys Ala Leu Ala Gly Leu Leu Leu Asn His Val Arg Gly Val Phe
            260                 265                 270

Lys Ala Val Ala Val Thr Ala Pro Gly Phe Gly Asp Lys Arg Pro Asn
        275                 280                 285

Arg Leu Leu Asp Leu Ala Ala Leu Thr Gly Gly Arg Ala Val Leu Glu
    290                 295                 300

Ala Gln Gly Asp Arg Leu Asp Arg Val Thr Leu Ala Asp Leu Gly Arg
305                 310                 315                 320

Val Arg Arg Ala Val Val Ser Ala Asp Asp Thr Ala Leu Leu Gly Ile
                325                 330                 335
```

-continued

```
Pro Gly Thr Glu Ala Ser Arg Ala Arg Leu Glu Gly Leu Arg Leu Glu
            340                 345                 350

Ala Glu Gln Tyr Arg Ala Leu Lys Pro Gly Gln Gly Ser Ala Thr Gly
        355                 360                 365

Arg Leu His Glu Leu Glu Glu Ile Glu Ala Arg Ile Val Gly Leu Ser
    370                 375                 380

Gly Lys Ser Ala Val Tyr Arg Val Gly Gly Val Thr Asp Val Glu Met
385                 390                 395                 400

Lys Glu Arg Met Val Arg Ile Glu Asn Ala Tyr Arg Ser Val Val Ser
                405                 410                 415

Ala Leu Glu Glu Gly Val Leu Pro Gly Gly Gly Val Gly Phe Leu Gly
            420                 425                 430

Ser Met Pro Val Leu Ala Glu Leu Glu Ala Arg Asp Ala Asp Glu Ala
        435                 440                 445

Arg Gly Ile Gly Ile Val Arg Ser Ala Leu Thr Glu Pro Leu Arg Ile
    450                 455                 460

Ile Gly Glu Asn Ser Gly Leu Ser Gly Glu Ala Val Val Ala Lys Val
465                 470                 475                 480

Met Asp His Ala Asn Pro Gly Trp Gly Tyr Asp Gln Glu Ser Gly Ser
                485                 490                 495

Phe Cys Asp Leu His Ala Arg Gly Ile Trp Asp Ala Ala Lys Val Leu
            500                 505                 510

Arg Leu Ala Leu Glu Lys Ala Ala Ser Val Ala Gly Thr Phe Leu Thr
        515                 520                 525

Thr Glu Ala Val Val Leu Glu Ile Pro Asp Thr Asp Ala Phe Ala Gly
    530                 535                 540

Phe Ser Ala Glu Trp Ala Ala Ala Thr Arg Glu Asp Pro Arg Val
545                 550                 555
```